(12) United States Patent
Blach et al.

(10) Patent No.: US 9,017,360 B2
(45) Date of Patent: *Apr. 28, 2015

(54) NASAL SUPPORT DEVICE AND METHOD

(71) Applicant: WinEase LLC, Eagan, MN (US)

(72) Inventors: Edward L. Blach, Roswell, NM (US); James R. Chiapetta, Delano, MN (US)

(73) Assignee: WinEase LLC, Eagan, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/331,423

(22) Filed: Jul. 15, 2014

(65) Prior Publication Data

US 2015/0039022 A1 Feb. 5, 2015

Related U.S. Application Data

(63) Continuation of application No. 14/012,282, filed on Aug. 28, 2013, now Pat. No. 8,795,314, which is a continuation of application No. 13/457,779, filed on Apr. 27, 2012, now Pat. No. 8,529,594, which is a continuation of application No. 12/848,810, filed on Aug. 2, 2010, now Pat. No. 8,182,505, which is a (Continued)

(51) Int. Cl.
*A61M 29/00* (2006.01)
*A61D 7/00* (2006.01)
*A61F 5/08* (2006.01)

(52) U.S. Cl.
CPC .... *A61D 7/00* (2013.01); *A61F 5/08* (2013.01)

(58) Field of Classification Search
USPC ............... 606/199, 201, 204.45; 128/200.24, 128/201.18
See application file for complete search history.

(56) References Cited

U.S. PATENT DOCUMENTS

| | | |
|---|---|---|
| 1,034,123 A | 7/1912 | Knowlson |
| 1,043,924 A | 11/1912 | Gottlieb |
| 1,232,956 A | 7/1917 | Mooney |
| 1,292,083 A | 1/1919 | Sawyer |
| 1,950,839 A | 3/1934 | Chirila |
| 2,335,936 A | 12/1943 | Hanlon |
| 2,515,756 A | 7/1950 | Bove |
| 3,007,571 A | 11/1961 | Marinaro |
| 3,214,502 A | 10/1965 | Schaar |
| 3,691,140 A | 9/1972 | Silver |
| 3,710,799 A | 1/1973 | Caballero |
| 4,153,051 A | 5/1979 | Shippert |
| 4,201,217 A | 5/1980 | Slater |
| 4,213,452 A | 7/1980 | Shippert |

(Continued)

FOREIGN PATENT DOCUMENTS

| | | |
|---|---|---|
| AU | A-65890/96 | 4/1998 |
| EP | 0 757 905 A1 | 2/1997 |

(Continued)

OTHER PUBLICATIONS

Amis et al., "Nasal vestibule wall elasticity: interactions with a nasal dilator strip," *J Appl Physiol* 86(5):1638-1643 (1999).

(Continued)

*Primary Examiner* — Victor Nguyen
(74) *Attorney, Agent, or Firm* — Merchant & Gould P.C.

(57) ABSTRACT

The present disclosure provides a device and method for facilitating air flow in the nasal passage of a domestic animal. The nasal support device (NSD) disclosed herein is useful for facilitating air flow during rest, physical exertion, respiratory ailment, etc. The NSD secures to the nose of a domestic animal to support the unsupported lateral vestibular walls of the nasal passages by lifting or stenting.

14 Claims, 15 Drawing Sheets

Related U.S. Application Data continuation of application No. 12/082,673, filed on Apr. 10, 2008, now abandoned, which is a continuation of application No. 11/233,942, filed on Sep. 22, 2005, now abandoned, which is a continuation of application No. 10/732,022, filed on Dec. 9, 2003, now abandoned, which is a continuation of application No. 09/264,464, filed on Mar. 8, 1999, now Pat. No. 6,823,864, which is a continuation-in-part of application No. 09/018,603, filed on Feb. 4, 1998, now Pat. No. 6,033,422, which is a continuation-in-part of application No. 08/843,741, filed on Apr. 21, 1997, now Pat. No. 5,913,873.

(56) References Cited

U.S. PATENT DOCUMENTS

| | | |
|---|---|---|
| 4,274,402 A | 6/1981 | Shippert |
| 4,414,977 A | 11/1983 | Rezakhany |
| 4,576,168 A | 3/1986 | Jalowayski |
| 4,614,183 A | 9/1986 | McCracken et al. |
| 4,638,043 A | 1/1987 | Szycher et al. |
| 4,646,731 A | 3/1987 | Brower |
| 4,674,133 A | 6/1987 | Oschner |
| 4,744,355 A | 5/1988 | Faasse, Jr. |
| 4,759,365 A | 7/1988 | Askinazy |
| 4,917,688 A | 4/1990 | Nelson et al. |
| 4,994,322 A | 2/1991 | Delgado et al. |
| 4,995,383 A | 2/1991 | Anderson |
| 5,088,483 A | 2/1992 | Heinecke |
| 5,132,118 A | 7/1992 | Mills |
| 5,266,402 A | 11/1993 | Delgado et al. |
| 5,306,271 A | 4/1994 | Zinreich et al. |
| 5,383,891 A | 1/1995 | Walker |
| 5,407,440 A | 4/1995 | Zinreich et al. |
| 5,421,816 A | 6/1995 | Lipkovker |
| 5,476,091 A | 12/1995 | Johnson |
| 5,502,108 A | 3/1996 | Silver et al. |
| 5,533,499 A | 7/1996 | Johnson |
| 5,533,503 A | 7/1996 | Doubek et al. |
| 5,546,929 A | 8/1996 | Muchin |
| 5,549,103 A | 8/1996 | Johnson |
| 5,550,127 A | 8/1996 | Pantano |
| 5,553,605 A | 9/1996 | Muchin |
| RE35,408 E | 12/1996 | Petruson |
| 5,611,333 A | 3/1997 | Johnson |
| 5,611,334 A | 3/1997 | Muchin |
| D379,513 S | 5/1997 | Ierulli |
| 5,653,224 A | 8/1997 | Johnson |
| 5,669,377 A | 9/1997 | Fenn |
| 5,706,800 A | 1/1998 | Cronk et al. |
| 5,718,224 A | 2/1998 | Muchin |
| 5,719,247 A | 2/1998 | Delgado et al. |
| 5,755,232 A | 5/1998 | Kalt |
| 5,765,548 A | 6/1998 | Perry |
| 5,769,089 A | 6/1998 | Hand et al. |
| 5,817,039 A | 10/1998 | Raunig |
| 5,842,469 A | 12/1998 | Rapp et al. |
| 5,890,486 A | 4/1999 | Mitra et al. |
| 5,913,873 A * | 6/1999 | Blach et al. ............... 606/204.45 |
| 5,947,119 A | 9/1999 | Reznick |
| 5,954,049 A | 9/1999 | Foley et al. |
| 5,957,126 A | 9/1999 | Resznick |
| 5,961,537 A | 10/1999 | Gould |
| 5,976,173 A | 11/1999 | Berke |
| 6,017,357 A | 1/2000 | Blach et al. |
| 6,029,658 A | 2/2000 | De Voss |
| 6,033,422 A | 3/2000 | Blach et al. |
| D422,703 S | 4/2000 | Lundy, Jr. et al. |
| 6,065,470 A | 5/2000 | Van Cromvoirt et al. |
| 6,080,179 A | 6/2000 | Gould |
| D429,332 S | 8/2000 | Ierulli |
| D430,295 S | 8/2000 | Ierulli |
| 6,098,616 A | 8/2000 | Lundy, Jr. et al. |
| D432,652 S | 10/2000 | Ierulli |
| 6,203,560 B1 | 3/2001 | Blach et al. |
| 6,228,037 B1 | 5/2001 | Derksen |
| 6,228,101 B1 | 5/2001 | Stratton |
| 6,318,362 B1 | 11/2001 | Johnson |
| 6,352,548 B1 | 3/2002 | Blach et al. |
| 6,375,667 B1 | 4/2002 | Ruch |
| 6,453,901 B1 | 9/2002 | Ierulli |
| 6,470,883 B1 | 10/2002 | Beaudry |
| 6,540,766 B2 | 4/2003 | Martino |
| 6,676,681 B1 | 1/2004 | Blach et al. |
| 6,823,864 B2 | 11/2004 | Blach et al. |
| 8,182,505 B2 | 5/2012 | Blach et al. |
| 8,529,594 B2 | 9/2013 | Blach et al. |
| 8,795,314 B2 * | 8/2014 | Blach et al. ............... 606/199 |
| 2003/0005938 A1 | 1/2003 | Lockwood |

FOREIGN PATENT DOCUMENTS

| | | |
|---|---|---|
| EP | 0 778 014 A1 | 6/1997 |
| EP | 1 033 118 A1 | 9/2000 |
| EP | 1 174 100 A2 | 1/2002 |
| EP | 1 402 858 A1 | 3/2004 |
| ES | 289561 | 10/1985 |
| FR | 363.758 | 8/1906 |
| GB | 768488 | 2/1957 |
| GB | 2313313 | 11/1997 |
| WO | WO 92/22340 | 12/1992 |
| WO | WO 94/23675 | 10/1994 |
| WO | WO 97/02793 | 1/1997 |
| WO | WO 97/42918 | 11/1997 |
| WO | WO 98/12998 | 4/1998 |
| WO | WO 98/25541 | 6/1998 |
| WO | WO 98/47451 | 10/1998 |
| WO | WO 99/37258 | 7/1999 |
| WO | WO 99/65430 | 12/1999 |
| WO | WO 01/60294 A1 | 8/2001 |

OTHER PUBLICATIONS

Art et al., "Effect of exercise on the partitioning of equine respiratory resistance," *Equine Vet J* 20(4):268-273 (Jul. 1988).

Art et al., "Mechanics of breathing during strenuous exercise in thoroughbred horses," *Respir Physiol* 82:279-294 (1990).

Bruintjes et al., "A Functional Anatomic Study of the Relationship of the Nasal Cartilages and Muscles to the Nasal Valve Area," *The Laryngoscope*, 108:1025-1032 (Jul. 1998).

Declaration of James R. Chiapetta re: Kev's World Cartoon.

Di Somma et al., "Nasal dilator strips increase maximum inspiratory flow via nasal wall stabilization," *The Laryngoscope* 109:780-784 (May 1999).

Erickson, "Exercise induced pulmonary haemorrhage," *Proceedings of the Fourth International Conference on Equine Exercise Physiology*, (Jul. 11-16, 1994) in *Equine Vet J Suppl* 18: 476-478 (1995).

Erickson et al., "Pulmonary artery, aortic and oesophageal pressure changes during high intensity treadmill exercise in the horse: a possible relation to exercise-induced pulmonary haemorrhage," *Equine Vet J. Suppl.* 9:47-52 (1990).

Erickson et al., "What Causes Racehorse Lungs to Bleed?," *The Quarter Racing J.*, 52-57 (May 1995).

Fedde et al., "Increase in blood viscosity in the sprinting horse: can it account for the high pulmonary arterial pressure?," *Equine Vet J.*, 30(4):329-334 (1998).

Foerner, "The Diagnosis and Correction of False Nostril Noises," *AAEP Proceedings*, pp. 315-327 (1967).

Funkquist et al., "Studies on the intratracheal pressure in the exercising horse," *J. Vet. Med A*, 35:424-441 (1988).

Gillespie, "The role of respiratory system during exertion," *J S Afr Vet Assoc* 45(4):305-309 (1974).

Goetz et al., "Pressures in the right side of the heart and esophagus (pleura) in ponies during exercise before and after furosemide administration," *Am J Vet Res* 47(2):270-277 (Feb. 1986).

Guillette, "Use of Nasal Valve Stent with Anterior Rhynomanometry to Quantitate Nasal Valve Obstruction," *Ann. Otol. Rhinol. Laryngol*, 99:175-178 (1990).

(56) References Cited

OTHER PUBLICATIONS

Haight et al., "The Site and Function of the Nasal Valve," *Laryngescope* 93:49-55 (Jan. 1983).

Hinchcliff, "Effects of furosemide on athletic performance and exercise-induced pulmonary hemorrhage in horses," *J Am. Vet. Med. Assoc.*, 215(5):630-635 (Sep. 1999).

Jackson et al., "Effects of airway obstruction on transmural pulmonary artery pressure in exercise horses," *Am J Vet Res* 58(8):897-903 (Aug. 1997).

Johnson et al., "Modelling exercise-induced pulmonary hemorrhage in racing thoroughbreds," *Frontiers Med Biol Eng* 4(4):271-289 (1992).

Jones et al., "The nasal valve: a physiological and clinical study," *J. of Laryngol. and Oto.*, 102:1089-1094 (Dec. 1988).

Kelley, B., "EIPH: What we know about bleeding," Equine Athlete, pp. 21-24, 26-27 (Mar./Apr. 1997).

Kev's World Cartoon (Exhibit 1).

Lekeux et al. "The respiratory system: anatomy, physiology, and adaptations to exercise and training," *The Athletic Horse*, DR Hodgson and RJ Rose (eds), WB Saunders (1994).

Manohar, "Furosemide attenuates the exercise-induced increase in pulmonary artery wedge pressure in horses," *Am. J. Vet. Res.*, 54(6):952-958 (Jun. 1993).

Manohar, "Furosemide attenuates the exercise-induced rise in pulmonary capillary blood pressure in horses," *Equine Vet. J.*, 26(1):51-54 (1994).

McKane et al., "Equine bronchoalveolar lavage cytology: survey of Thoroughbred racehorses in training," *Aust. Vet. J.*, 70(11):401-404 (Nov. 1993).

Meyer et al., "Quantification of exercise-induced pulmonary haemorrhage with bronchoalveolar lavage," *Equine Vet. J.*, 30(4):284-288 (1998).

Olsen et al., "Influence of furosemide on hemodynamic responses during exercise in horses," *Am. J. Vet. Res.*, 53(5):742-747 (May 1992).

Robinson et al., "Pathophysiology of airway obstruction in horses: A Review," *J Am Vet Med Assoc* 172(3):299-303 (Feb. 1978).

Roithmann et al., "Acoustic Rhinometric Assessment of the Nasal Valve," *American Journal of Rhinology*, 11(5):379-402 (1997).

Sinha et al., "Pleural pressure changes during exercise do not affect measurement of mean vascular pressures," *Equine Vet. J. Suppl.*, 18:95-98 (1995).

Whitwell et al., "Collection and evaluation of tracheobronchial washes in the horse," *Equine Vet. J.*, 16(6):499-508 (1984).

\* cited by examiner

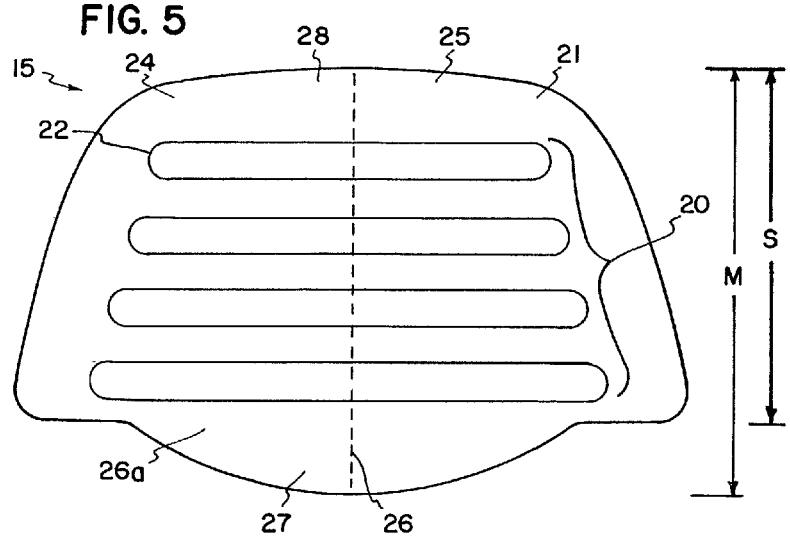
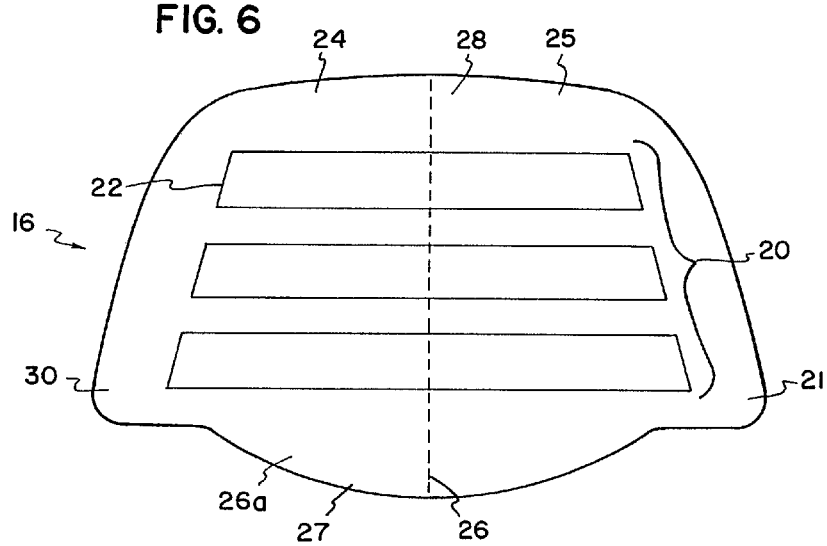

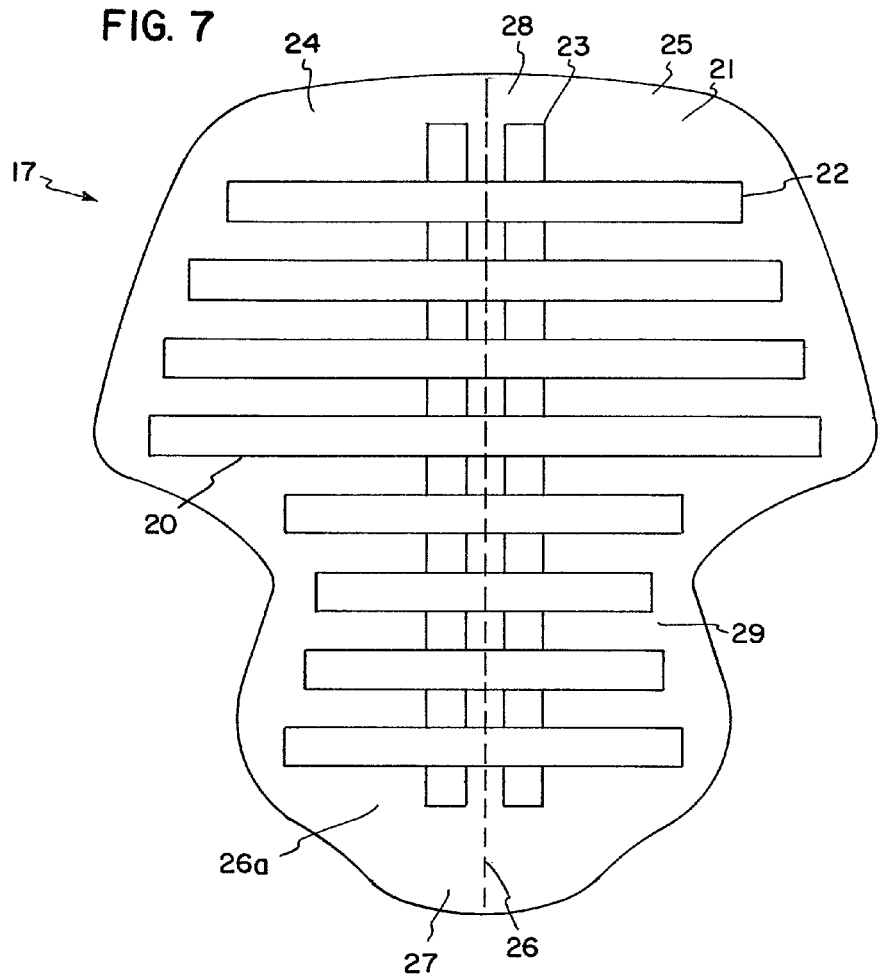

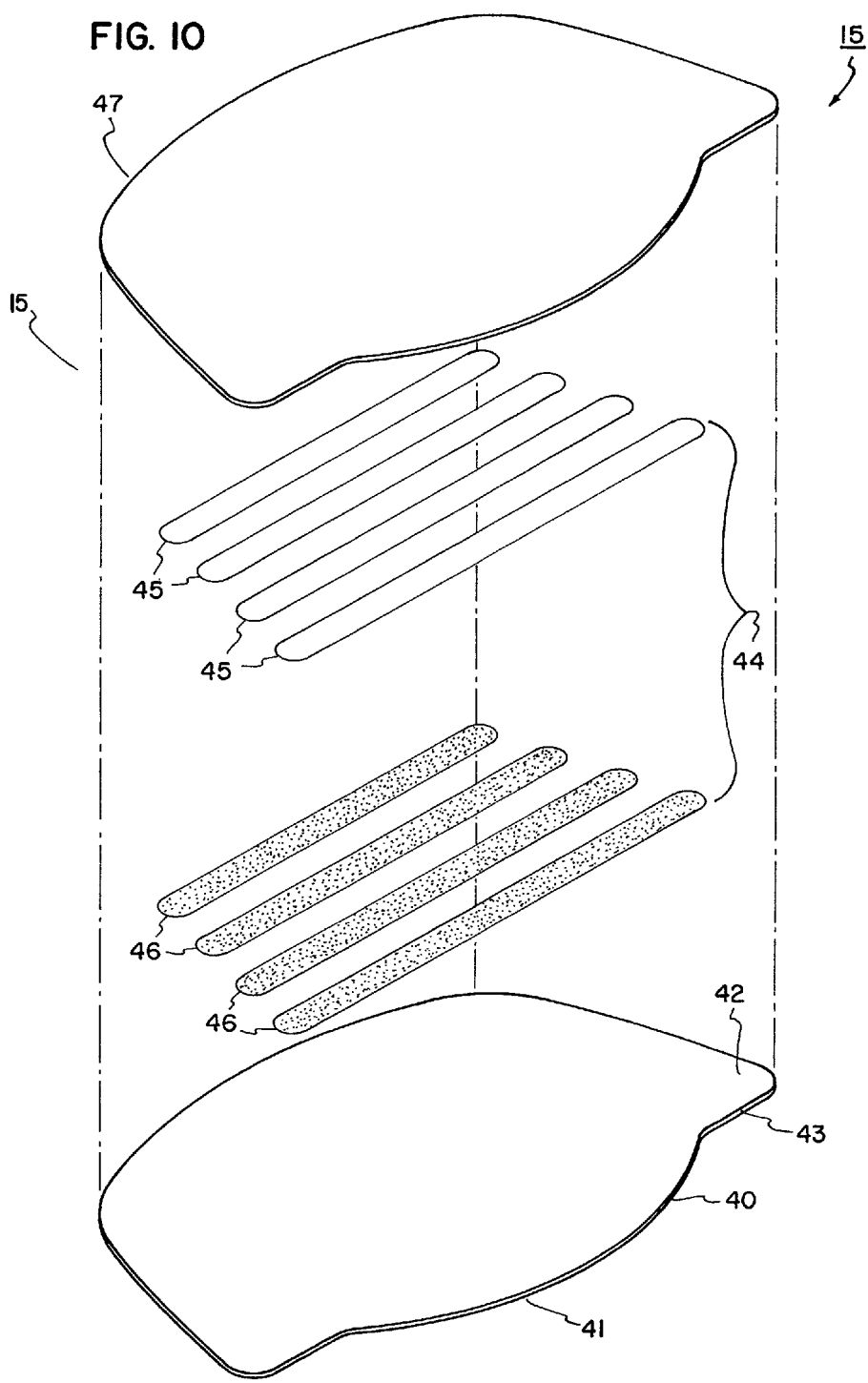

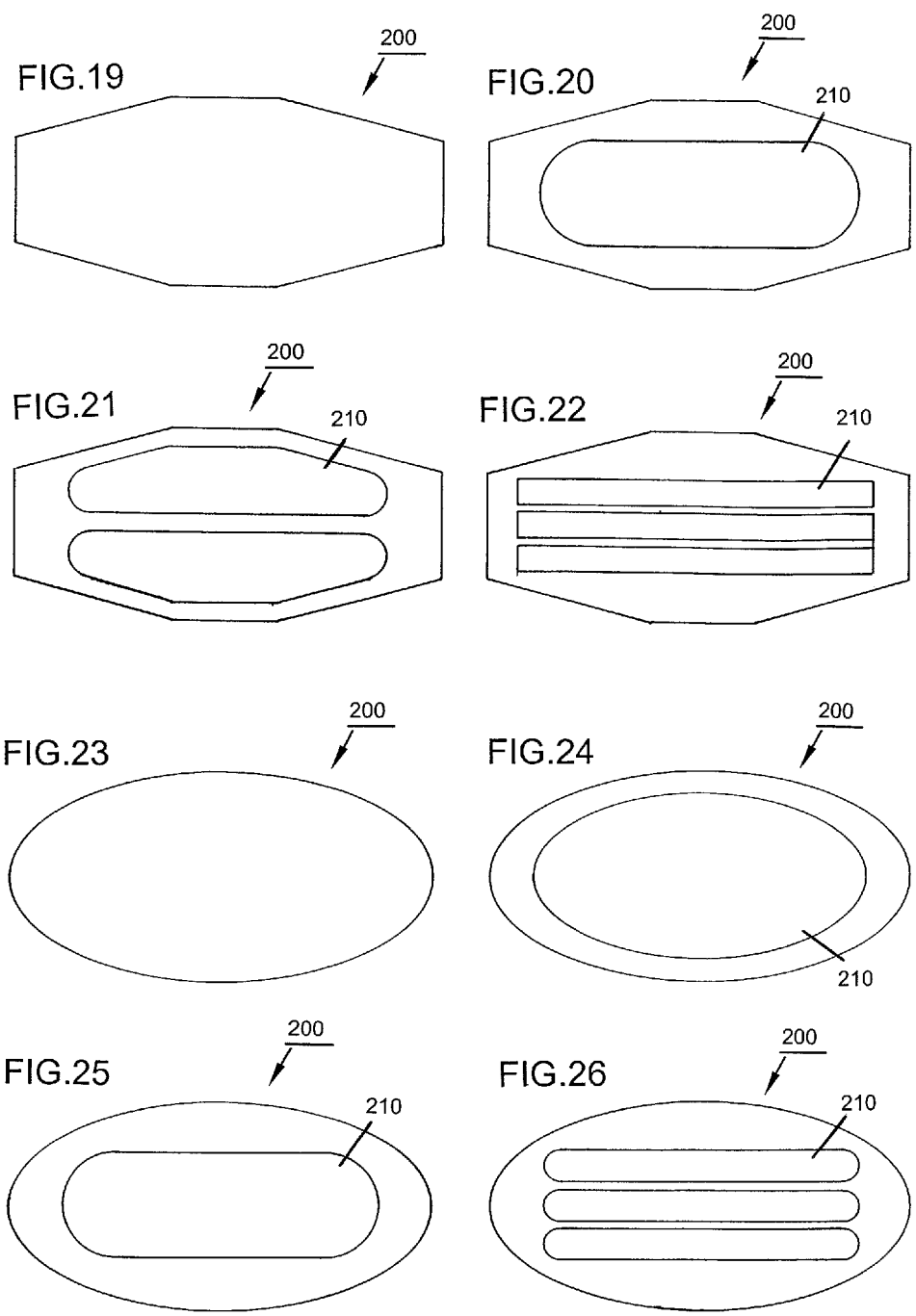

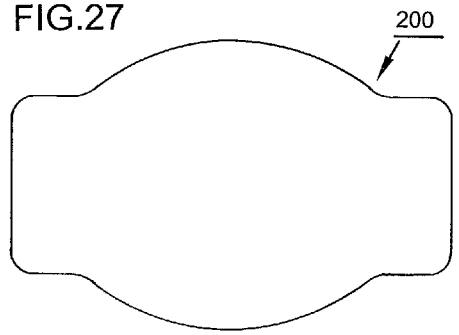
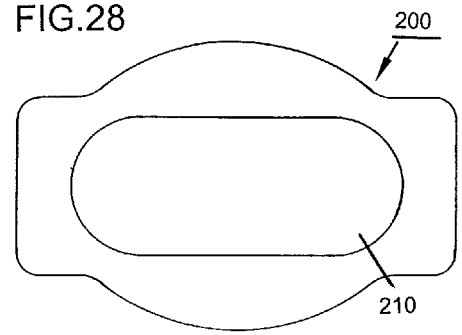
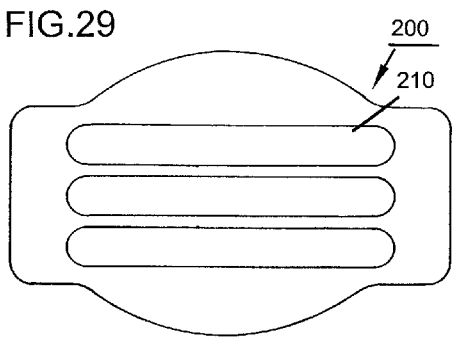
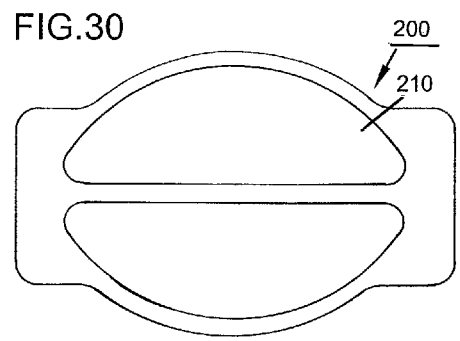
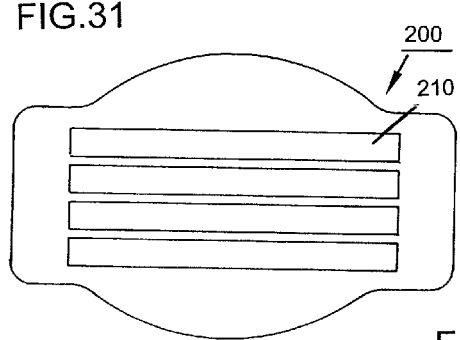
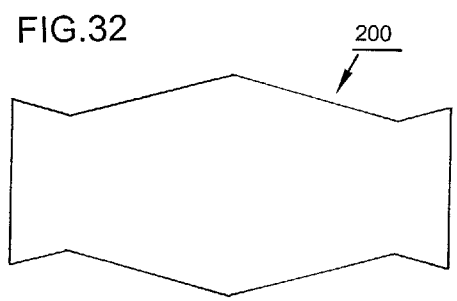
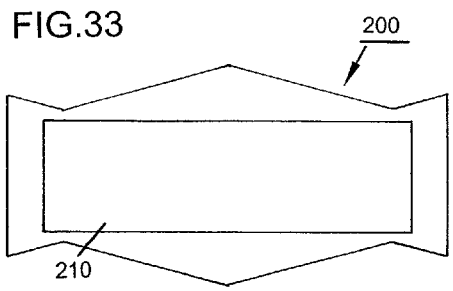

NASAL SUPPORT DEVICE AND METHOD

CROSS-REFERENCE TO RELATED APPLICATION

The present application is a continuation of U.S. patent application Ser. No. 14/012,282, filed Aug. 28, 2013, which is a continuation of U.S. patent application Ser. No. 13/457,779, filed Apr. 27, 2012, now U.S. Pat. No. 8,529,594, which is a continuation of U.S. patent application Ser. No. 12/848,810, filed Aug. 2, 2010, now U.S. Pat. No. 8,182,505, which is a continuation of U.S. patent application Ser. No. 12/082,673, filed Apr. 10, 2008, now abandoned, which is a continuation of U.S. patent application Ser. No. 11/233,942, filed Sep. 22, 2005, now abandoned, which is a continuation of U.S. patent application Ser. No. 10/732,022, filed Dec. 9, 2003, now abandoned, which is a continuation of U.S. patent application Ser. No. 09/264,464, filed Mar. 8, 1999, now U.S. Pat. No. 6,823,864, which is a continuation-in-part of U.S. patent application Ser. No. 09/018,603, filed Feb. 4, 1998, now U.S. Pat. No. 6,033,422, which is a continuation-in-part of U.S. patent application Ser. No. 08/843,741, filed Apr. 21, 1997, now U.S. Pat. No. 5,913,873, the entire disclosure of each of these applications being incorporated herein by reference.

FIELD OF THE INVENTION

The present invention is directed to facilitating air flow through the nasal passages of a domestic animal. Specifically, the invention provides devices and methods for supporting the soft tissue structures of the nasal passages of a domestic animal.

BACKGROUND OF THE INVENTION

Portions of the following discussion of the nasal anatomy of domestic mammals are excerpted from R. Nickel et al., *The Viscera of Domestic Animals*, (2nd revised ed.), Springer-Verlag, New York, Hiedelberg, Berlin (1979), pp. 211-221. This is an excellent text on the comparative visceral anatomy of domestic mammals. As used herein, the terms "mammal" and "animal" are used synonymously and refer to non-human mammals.

The nasal anatomy of domestic animals is considerably different than that of a human. Unlike the human nose that projects distinctly from the face, in domestic animals, the nose is incorporated into the face and forms the large dorsal and lateral areas rostral to the eyes. The nostrils in the apex of the nose are the entry to the respiratory system of domestic mammals. Once passing through the nostrils, inspired air moves into the nasal cavities and continues through the nasopharynx, larynx, trachea and lungs.

At the apical entrance to the nose the nostrils are partitioned by the nasal septum to divide the nasal cavity into right and left halves. The caudal portion of the septum is bony, while rostrally the septum consists of cartilage which becomes progressively more flexible toward the apex.

The wall of the nose consists of skin externally and a middle supporting layer of bone caudally and cartilage rostrally. The nasal cavity is lined by a mucous membrane. The rostral bones forming the wall of the nose include the nasal, maxillary and incisive bones. The free borders of the nasal and incisive bone provide attachment for the cartilages which support the nostrils. The supporting bones and cartilages of the nose are associated with the nasal muscles that regulate the size of the nostrils.

The dorsal and ventral lateral nasal cartilages are formed by the widening of the rostral part of the nasal septum along its dorsal and ventral margins. In the horse, the ventral lateral nasal cartilage is small and may be absent. In many domestic animals, there is no lateral support for the soft tissue over the rostral nasal passage caudal to the nostril.

A further difference in the formation of the nasal cartilages of the horse is the presence of alar cartilages. The alar cartilages consist of a ventral cornu and a dorsal lamina and support the nostrils dorsally, medially and ventrally. The lamina of the alar cartilage and the medial accessory cartilage support the nasal diverticulum, a blind pouch in the dorsal aspect of the nostril.

The muscles of the nose and upper lip act to dilate the nostrils. This is particularly noticeable during labored breathing. In the horse, these muscles are well developed and can transform the normally semilunar nostrils to become circular.

The dorsal lateral area of the rostral nasal cavity that is caudal to the alar cartilages in the nostrils of the horse includes a region of unsupported soft tissue which can be drawn into the nasal cavity during inspiration of air into the nasal passages. The nasal diverticulum of the horse is a part of the soft tissue structures of the horse which can be drawn into the nasal cavity. When the soft tissue is drawn in, it can narrow the nasal cavity and reduce the area for the intake of air, thus reducing the air movement into the nasal passages and ultimately to the lungs where the oxygen is transferred in the pulmonary aveoli. The physiological effects of reduced oxygen transfer at rest and during physical exertion are documented. Some experts have theorized that exercise induced pulmonary hemorrhage (EIPH) in performance horses is caused by asphyxia due to abnormal resistance of a closed or partially closed upper airway. The upper airway being defined as the region of the respiratory tract lying between the nostrils and the windpipe at the level of the first rib. Hence, the nasal passages are part of this region. Dr. Robert Cook, "EIPH or AIPE? A Tufts University Researcher suggests that bleeding is not caused by EIPH, but by asphyxia", *The Equine Athlete*, p. 22-23 (March/April 1997).

Devices for dilating the outer wall tissue of the nasal passages in humans have been described in, for example, U.S. Pat. Nos. 5,533,503; 5,546,929; 5,553,605; and RE 35,408. These devices, however, do not address the unique soft tissue structures and mechanical problems associated with providing support for the nasal tissues of non-human mammals, especially large performance mammals such as the horse and camel.

Accordingly, there is a need to reduce the detrimental effects of reduced air intake, or to enhance the physiological benefit of increased air intake, during physical exertion of domestic mammals. Specifically, there is a need to increase, or reduce the decrease of, nasal passage narrowing that can occur during breathing in domestic mammals, especially performance animals such as the horse, camel, and dog.

SUMMARY OF THE INVENTION

The present invention provides devices and methods for using the devices to support the unsupported nasal tissues of a domestic animal. The invention addresses providing support in view of the structural and physiological characteristics unique to the nose of a non-human animal, for example, a horse. In some embodiments, a nasal support device (NSD) disclosed herein can reduce inspiratory air flow impedance by at least about 5-10%

In one embodiment the invention is a NSD for securing to the nose of a domestic animal. The NSD provides support to the right and left lateral vestibular walls of a domestic animal. The device includes a support layer and a right and left side piece which when secured to the nose of the animal are positioned to provide structural support to the right and left lateral vestibular walls. The side pieces of the device can meet at the midline region of the device. When secured to the nose of a domestic animal, the midline region of an NSD of the invention straddles the left and right nasal bones of the animal.

The sides and the midline region of the NSD each have a rostral end, a caudal end and a rostral-poll dimension. In one embodiment, the rostral-poll dimension of the midline region is at least as great as either of the rostral-poll dimensions of the side pieces. In an alternative embodiment, the rostral-poll dimension of the midline region is greater than either of the rostral-poll dimensions of the side pieces. In some embodiments, the rostral-poll dimension at the midline region is greater than either of the rostral-poll of the side pieces and the device is bilaterally symmetrical across both the longitudinal and transverse axes of the device. In some embodiments, the rostral end of the NSD can extend rostrally between the nostrils in the form of a "tongue" to provide externalizing support to the soft tissues between the nostrils.

An NSD configured according the invention can be used on many different animals. In one embodiment an NSD is sized to fit a member of the Equidae family, including the domestic horse. The device is suitable for adults and young animals. In general, the structural aspects of an NSD of the invention can be configured and sized to fit the nose of, for example, a dog, human, horse, camel, etc.

In general, an NSD comprises a support layer, an engaging layer, and in some embodiments a surface layer and/or pad layer. The support layer of an NSD can include one or more lift members to support the vestibular wall. The lift members can traverse the nose and extend to a point dorsal to the ventral border of the vestibular wall, or beyond the ventral border of the vestibular wall lateral to the incisive bone. Alternatively, one or more lift members of an NSD can be applied over each vestibular wall and act to externally stent each vestibular wall independently without connecting to one another across the midline of the nose.

The invention further provides a method for supporting a first and second vestibular free wall of a domestic animal by securing a device which supports the first and second vestibular free walls to the nose of the animal. In one embodiment, the method includes use of an NSD as disclosed herein.

The method of the invention provides for facilitating air flow through the nasal passages of a domestic animal. The device and method of the invention are particularly advantageous for use in the horse and are beneficial for facilitating athletic performance or for reducing the occurrence, severity or affect(s) of respiratory diseases in an adult or young animal.

A device and method according to the invention can be used on an animal that is running freely in a pasture, or wearing saddlery, harnesses or other equipment that can be attached to the nose of the animal.

BRIEF DESCRIPTION OF THE DRAWINGS

FIG. 5 is a top plan view of one embodiment of an NSD with the surface layer removed and the support layer exposed.

FIG. 6 is a top plan view of a second embodiment of an NSD with the surface layer removed and the support layer exposed.

FIG. 7 is a top plan view of a third embodiment of an NSD with the surface layer removed and the support layer exposed.

FIG. 10 is an exploded perspective view of the components of the embodiment of an NSD configured as shown in FIG. 5.

FIG. 19 is an alternative embodiment of a top side view of an NSD having two axes bilateral symmetry;

FIG. 20 is bottom side view of the NSD of FIG. 19;

FIG. 21 is an alternative embodiment of a bottom side view of the NSD of FIG. 19;

FIG. 22 is an alternative embodiment of a bottom side view of the NSD of FIG. 19;

FIG. 23 an alternative embodiment of a top side view of an NSD having two axes bilateral symmetry;

FIG. 24 is bottom side view of the NSD of FIG. 23;

FIG. 25 is an alternative embodiment of a bottom side view of the NSD of FIG. 23;

FIG. 26 is an alternative embodiment of a bottom side view of the NSD of FIG. 23;

FIG. 27 an alternative embodiment of a top side view of an NSD having two axes bilateral symmetry;

FIG. 28 is bottom side view of the NSD of FIG. 27;

FIG. 29 is an alternative embodiment of a bottom side view of the NSD of FIG. 27;

FIG. 30 is an alternative embodiment of a bottom side view of the NSD of FIG. 27;

FIG. 31 is an alternative embodiment of a bottom side view of the NSD of FIG. 27 FIG. 32 an alternative embodiment of a top side view of an NSD having two axes bilateral symmetry;

FIG. 33 is bottom side view of the NSD of FIG. 32;

DETAILED DESCRIPTION OF THE INVENTION

Figure 1A:
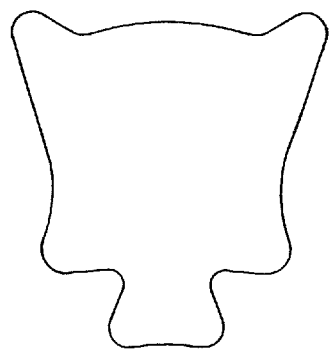
FIG. 1a is a top view of one configuration of an embodiment of an NSD which incorporates the functional aspects of the invention.
Figure 1D:
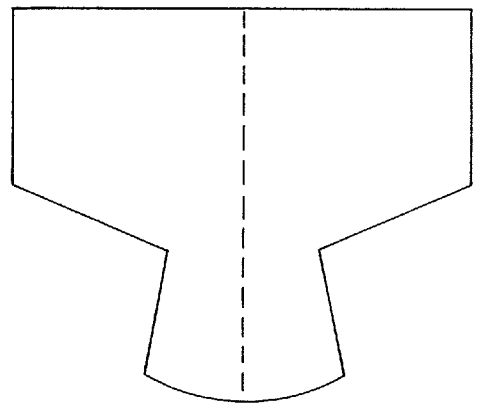
FIG. 1d is a top view of a fourth configuration of an embodiment of an NSD which incorporates the functional aspects of the invention.
Figure 1B:
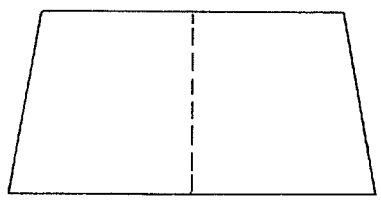
FIG. 1b is a top view of a second configuration of an embodiment of an NSD which incorporates the functional aspects of the invention.
Figure 1E:
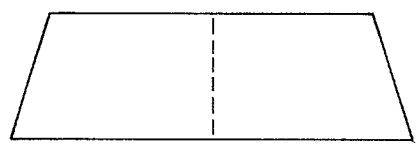
FIG. 1e is a top view of a fifth configuration of an embodiment of an NSD which incorporates the functional aspects of the invention.

The invention is directed to devices and methods for supporting the soft tissue at the rostral aspect of the nasal cavity of domestic mammals. Specifically, the devices and methods disclosed herein provide support for the unsupported region of the "vestibule" in the rostral nasal cavity.

As used herein, domestic mammals include most non-human production and performance animals having a nose incorporated into the face, rather than projecting therefrom, that can benefit from a device according to the invention. Such mammals include dogs, sheep, goats, cattle, horses, camels, llamas, etc. A device according to the invention can be particularly useful for members of the Equidae family including horses, donkeys, mules, zebras etc.

As used herein, "performance activities" or "work" includes activities such as pulling, driving, racing (flat, steeple, barrel, etc.), eventing, hunting, jumping, rodeoing, trail riding, endurance riding, etc. In general, the device can be used anytime it is desired to facilitate or enhance nasal air intake. In addition, to facilitating air flow, an NSD according to the invention can also be used to treat or prevent respiratory ailments in adult or young animals such as foals and calves. It is foreseen that the devices and methods of the invention may be particularly beneficial in horses for reducing the severity or affect(s) of laryngeal hemiplegia, chronic obstructive pulmonary disease (COPD) or exercise related pathologies such as myositis, dorsal displacement of the soft palate (DDSP), or exercise induced pulmonary hemorrhage (EIPH) or "bleeding".

As used herein, the term "rostral" refers to that aspect of the nose or anatomical structure closest to the apex of the nose. "Caudal" refers to that aspect of the nose closest to the poll or caudal aspect of the head relative to the apex. The "vestibule" refers to the rostral aspect of the nasal cavity that is defined by the alar cartilages rostrally, the incisive bone ventrally, the nasal bone dorsally, the caudal intersection of the incisive and nasal bones caudally, and the nasal septum medially. Thus, supported regions of the vestibule are supported by bone or cartilage.

The "unsupported" region of the vestibule is also referred to as the "lateral (free) wall" of the vestibule or "vestibular wall". The lateral wall of the vestibule includes the unsupported soft tissue defined by the nostrils rostrally, the lateral free border of the nasal bone dorsally, the dorsal free border of the incisive bone ventrally, and the intersection of the nasal and incisive bone caudally. In the horse, the dorsal border of the unsupported region can include the dorsal lateral nasal cartilage and, in some species, the ventral border can include the ventral lateral nasal cartilage. Herein, "soft tissue" has its general meaning including skin, muscle, fat, connective tissue or associated integumentary structures.

In general, the anatomy of soft muzzled mammals such as the horse and camel give rise to unique physical mechanical problems in supporting the vestibular soft tissues. For example, in the horse, the alar cartilages that are attached at the rostral border of the nasal septum supports the alar fold which gives rise to the blind cutaneous pouch referred to as the "false" nostril. Providing structural support for the vestibule of the horse preferably includes providing support of the alar fold. A suitable support device according to the invention, preferably causes minimal irritation to the skin or other anatomic structures of the animal when in use or after removal.

Other anatomical and physiological characteristics of a soft muzzle animal must be overcome to provide a suitable NSD for these animals. For example, the hair that covers the external vestibular tissues can reduce the ability of an NSD to remain adhered to the animal's nose under certain conditions. In addition, the presence of numerous sweat glands in this region, with or without the presence of hair, can also significantly reduce the ability of an NSD to remain adhered to this region when the animal is perspiring.

A further unique characteristic is the significant mobility of the external soft tissues in the vestibular region of some animals. For example, the muscular anatomy associated with the vestibular wall and nostrils of the horse enables considerable flexion, extension, twisting and side-to-side motion of the external vestibular tissues. The repeated in and out movement of the vestibular tissues during inspiration and expiration also affects the ability of an NSD to maintain a functional position in these animals. Thus, the combination of hair, sweat and vestibular wall movement during intense exercise present unique challenges to adherence and functioning of an NSD in certain animals, such as the horse.

Another factor considered in providing an NSD for support of the vestibule of a horse or camel is the equipment, including saddlery or harnesses, worn by the animal when working. Generally, "saddlery" refers to bits, bridles, martingales, muzzles, headcollars, saddles and other equipment used with a riding animal. "Harness" refers to equipment used with a driving animal. A suitable configuration and arrangement of an NSD of the invention preferably does not interfere with the functioning of saddlery or harnesses and the saddlery or harnesses preferably do not interfere with the functioning of the NSD.

It should be noted that an NSD according to the present invention need only engage the lateral free wall of the vestibule, it does not need to engage the nostrils. Upon visual inspection it will be appreciated that the nostril of the horse can expand to a cross-sectional area that is greater than an unsupported cross-sectional area measured in the nasal cavity in the region of the lateral vestibular wall. However, it is foreseen that support of the nostril could be provided in some circumstances. In the horse, for example, the muscles of the nose and upper lip generally provide significant flaring of the nostril during labored breathing.

Some exemplary embodiments of a device of the invention and its components are described below. Throughout the specification guidance is provided by examples of representative groups, the groups are not meant to be limiting.

The configuration and arrangement of an NSD of the invention is determined by the configuration of the tissue to be supported, the amount of support needed and the unique physiological or anatomical characteristics of the animal. Generally, the unique nasal anatomy of domestic animals necessitates configurations, arrangements or dimensions which are different than that required for a human nose. In addition, as discussed previously, hair, sweat and vestibular wall mobility affect the structural arrangement necessary for functionality of an NSD.

In a typical embodiment, a herein disclosed NSD provides support to the right and left lateral vestibular walls of the animal. Generally, the device includes a support layer having a right and left side piece which when secured to the nose of the animal are positioned to provide structural support to the right and left lateral vestibular walls. The "right" and "left" side pieces can also be referred to as "first" and "second" or "second" and "first" side pieces. The NSD is generally bilaterally symmetrical and does not utilize a narrow intermediate section between the side pieces. The side pieces of the device meet at about the midline a midline region of the device. When the NSD is secured to the nose of a domestic animal, the intersection of the right and left side pieces at the midline region substantially straddles the left and right nasal bones of the animal.

The side pieces and the midline region of an NSD each have a rostral end, a caudal end and a rostral-poll dimension. Because of the size and related anatomy of the surface area of the vestibular free wall of, for example a horse, to provide sufficient support to benefit the animal, the rostral-poll dimension at the midline region of an NSD of the invention can be substantially equal to or greater than the rostral poll dimension of the side pieces that engage the vestibular free wall. Hence, in one embodiment, the rostral-poll dimension of the midline region is at least as great as the rostral-poll dimension of either of the side pieces. In an alternative embodiment, the rostral-poll dimension of the midline region is greater than the rostral-poll dimension of the right or left side piece. However, a device having a relatively narrow intermediate region similar to some devices available for humans, and modified to include an increased surface area, modified support system and modified adhesive system may provide some benefit to an animal.

In addition, it is foreseen, that although the preferred configuration of an NSD of the invention is particularly advantageous for use on animals such as horses, the unique configurations disclosed herein can provide an advantageous improvement in dilators for a human nose. Moreover, a device having the general configuration of a preferred embodiment of the invention, but sized for use with a human nose, can also advantageously provide a sun blocking, or visor effect, for the proximal and/or rostral end of a human nose. Two configurational embodiments particularly suited for a human or animal nose are illustrated in FIG. 1h and 1i. In one preferred embodiment for humans, at least two lift members of 1400A Gauge MYLAR®, available from DuPont Films, Wilmington Del., are applied transversely as support members in an NSD configuration such as that illustrated in FIG. 1h.

In some embodiments, the rostral end of the NSD at or near the midline region extends to the apex of the muzzle between the nostrils and is referred to as a "tongue". This embodiment can provide lift support to the most rostral aspect of the soft tissues and cartilaginous nasal septum between the nostrils.

The structural configuration and arrangement of an NSD can vary in some aspect(s) and still maintain the mechanical functioning of a device according to the invention. Personalization of the external design of an NSD can reflect aesthetics, personal tastes, racing colors, etc. The overall appearance of the embodiments illustrated in the present disclosure are not exhaustive of those which are within the scope of the invention. Examples of a few general configurations which impart some or all of the functional aspects of the invention are shown in the top plan views of FIG. 1a-i, and 5-13. Generally the bottom plan configuration of an NSD is substantially identical to the top plan configuration shown. The side plan view is substantially void of ornamental features.

As used herein, the term "support" refers to reducing the amount of narrowing of the nasal passage that can occur during inspiration or expiration of domestic animals. Accordingly, "support" can include some drawing in of the vestibular free wall at the rostral nasal passage during inspiration, but less than that which would occur without a device of the invention. "Support" also includes maintaining the position of the external soft tissue over the rostral nasal passage in a neutral position. As used herein, "neutral" refers to a state where the unsupported vestibular tissues are neither drawn into the nasal cavity nor protruding externally relative to a resting position. In some arrangements, "support" also includes maintaining the vestibular free wall in a "distended" outward position relative to the neutral position.

The configuration and arrangement of a support device for animals takes into account the anatomical and physiological characteristics of the vestibular free wall as well as the bony structures defining its borders. Moreover, in most large domestic animals, the structural support necessary to support the lateral free wall must also take into account the weight of the tissue supported and the proper leveraging for distributing the weight supported without causing pressure sores or other irritation to surrounding tissues. In addition, due to the muscle control of the upper lip of the horse, supporting the vestibular free wall must also address the active and passive mobility of the muzzle structures.

The size of a device of the invention can vary. Appropriate sized devices will typically correspond with muzzle size which can vary with the body size, breed, age, and sex, of the animal. It is foreseen that smaller size NSDs for young animals, such as calves and foals can be beneficial in treating, for example, upper respiratory ailments. In some embodiments, the rostral-poll midline dimension of an NSD for an average sized adult horse is about 3 to 16 cm, preferably 6-14 cm and the rostral poll dimension of the right and left side is about 3 to 12 cm. However, larger and smaller sizes may be used.

The transverse dimension of an NSD can also vary. The "transverse dimension" is defined as the length of the device from the peripheral edge of one side of the device to the peripheral edge of the second side of the device. The transverse dimension can be approximately equal at the rostral and caudal edge. Alternatively, the transverse dimension can vary in a single device depending if measured, for example, along the caudal edge, the rostral edge, the narrowest part or the widest part. In one embodiment of an NSD for an average size horse, the transverse dimension at the narrowest part can be about 5-12 cm and about 10-17 cm at the widest part.

Typically, an NSD according to the invention includes at least a "support layer" and an "engaging layer". In some embodiments a "surface layer" can be present to cover the side of the support layer that is away from the nose of the animal when the device is secured to the nose of the animal. Some embodiments can also include one or more "pad layers" which can help reduce the chance of pressure sores caused by the device.

The support layer provides the majority of the support for the vestibular free wall of the nasal passage of an NSD. Generally, support is provided in the support layer through the use of one or more "lift members." As used herein a "lift member" can be prepared from any suitable material which provides the desired support to the vestibular free wall. Examples of suitable materials for a lift member include thermoplastic resins, thermoset resins, shape memory metals, alloys, leather, etc. The lift member can be a unitary open mesh or solid material. Alternatively, the lift member can be two or more individual sections of an open mesh or solid material. A preferred thermoplastic resin for a lift member is a polyester such as MYLAR® available from DuPont Films, Wilmington Del.

In some embodiments, the lift members are of a generally uniform thickness throughout their length and width. The thickness of the lift members will typically be selected based on the support needed, and is generally the same throughout. However, the lift member can also vary in thickness in different regions of the device. In addition, a lift member need not be the same width throughout its length. That is, the lift member can be wider at the lateral ends of the lift member. Alternatively, a lift member can be wider in the region that will lie over the midline region of the nose and narrower on the ends.

Suitable thickness for a lift member prepared from a polyester such as MYLAR® for an adult large animal such as a horse is about 0.008 to about 0.020 inches. In one preferred embodiment, the thickness of a support member for an average size adult horse is about 0.014 inches.

The support layer can include one or more lift members. In one embodiment using a single lift member, the configuration of the peripheral edge of the lift member can define the external contours of the overall device. In other embodiments, two and preferably, three or more lift members are used. In such embodiments, a plurality of lift members can be arranged parallel along the transverse dimension of the device. Alternatively, a plurality of lift members can be oriented perpendicular to one another such that one or more lift members are oriented parallel to the transverse dimension of the device and one or more lift members are oriented parallel to the rostral-poll dimension of the device. In yet another embodiment, two or more lift members can be oriented in a substantially criss-cross arrangement to form an "X" shaped appearance in top plan view.

In some embodiments it is advantageous to provide lift members in a rostral caudal direction. Lift members oriented in a rostral caudal direction can be located in the side pieces to further provide the lift of the NSD. In addition, or alternatively, lift members can be oriented in a rostral caudal direction at or near the midline intersection of the first and second side pieces. This arrangement of the lift members is particularly advantageous for NSD embodiments which extend rostrally to form a "tongue" for support of the soft tissue between the nostrils.

When using multiple solid lift members, the spacing between individual lift members can affect the adherence and overall functioning of an NSD. Appropriate spacing between individual lift members provides for the device to adaptively conform to the changing contours of the vestibular wall of an animal during inspiration, expiration or other movements, without disengaging from the animal's nose.

The width, length and spacing of one or more lift members can vary based on the overall dimensions of the particular NSD. Also, the length of the individual lift members can vary in a single device so as to traverse some or all of the dorsal-ventral dimension of the vestibular free wall. Preferably, the transverse length dimension of a lift member is sufficient to traverse the midline of the animal's nose and extend to the right and left side pieces beyond the dorsal lateral nasal cartilages to support the right and left vestibular free walls. In some embodiments, the lift members can extend beyond the ventral edge of to the vestibular free wall to a point lateral to the incisive bone. Generally, the lift members provide a "lift" effect on the vestibular free wall to reduce drawing of the vestibular free wall into the nasal passage during respiration. However, if the lift members extend beyond the ventral edge of the vestibular free wall to the lateral aspect of the incisive bone, the incisive bone can act with the lift members to "stent" the vestibular free wall and facilitate the reduction of the drawing of the vestibular wall into the nasal cavity that is provided by the lift members. This may be particularly advantageous in large animals during labored breathing.

When two or more lift members are used, the width of the lift members and the spacing between lift members are selected for the NSD to provide the desired support to the vestibular wall with sufficient flexibility to reduce the chance of irritation due to localized pressure at leveraging points on the animal's nose. In addition, use of multiple lift members provides for torsional flexibility of the device which helps maintain the functioning of the device when subjected to the unique mobility of an animals vestibular tissues. In one embodiment of an NSD for an average size adult horse, the length of the lift members can be about 4-18 cm, preferably about 9-12 cm, the width can be about 0.2 to 2 cm and the spacing between lift members about 0.2 to 2 cm, preferably about 0.3 to 0.7 cm.

In one embodiment, the lift member can be a single member of a previously described solid or open mesh material that is shaped to stent a single vestibular wall. That is, the outer contours of the lift member are configured to follow the peripheral margins of the vestibular wall. Preferably, the perimeter edge of the lift member is extended to allow the lift member to overlap the borders of the vestibular wall by about 0.2-2 cm. According to this embodiment, the lift member can include an engaging layer and optionally a surface or pad layer as described below. Preferably, the engaging layer can extend beyond the perimeter of the lift member to enhance adherence to an animal's nose. However, rather than connecting at the midline region of the nose, this embodiment of an NSD comprises two separate pieces, that act as a stent for each vestibular wall.

An NSD preferably includes an engaging layer. The engaging layer provides for securing an NSD to the animal. If no surface layer (described below) is present and individual lift members are used, the engaging layer can also provide for maintaining the unity of the device. Typically, the engaging layer can secure the NSD to the nose by use of an adhesive. Other invasive forms of engaging to the nose, such as suturing, are possible but not desired. Preferably, the adhesive is biocompatible and provides minimal or no contact irritation when applied to the external tissues of an animal.

Suitable materials for the adhesive of the engaging layer are single or double coated medical tape, transfer adhesives, or liquid adhesives. A release liner is preferably applied to the NSD to protect the adhesive surface of the engaging layer until application to an animal. Pressure sensitive adhesives (PSA) can be used. Examples of suitable adhesive systems are No. 1509 double sided medical tape and No. 9942 Hydrocolloid Skin Protective Adhesive available from 3M Co., St. Paul, Minn. A preferred adhesive system is No. 1524 transfer adhesive available from 3M Co., St. Paul, Minn. The adhesive can be continuous over the surface of the engaging layer.

Figure 11:
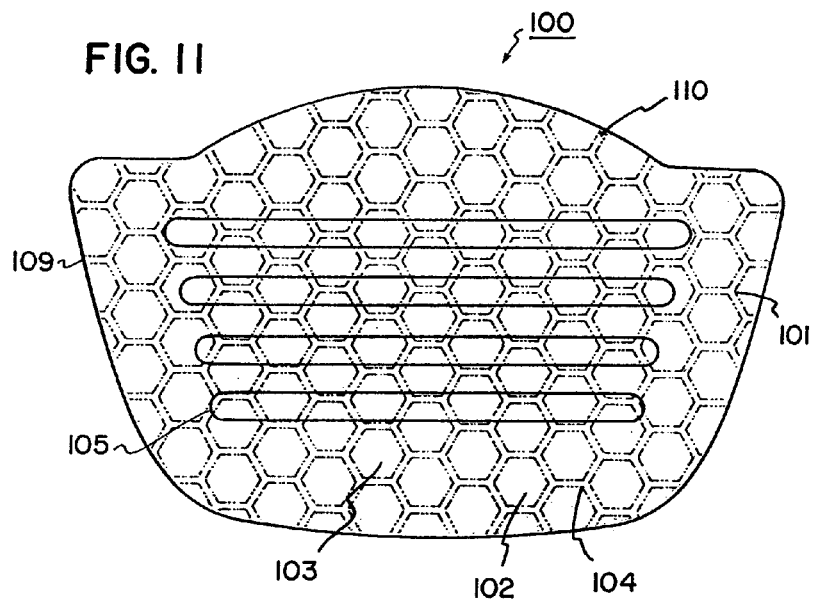
FIG. 11 is a bottom plan view of an engaging layer of an embodiment of an NSD having a discontinuous adhesive pattern.

Alternatively, the adhesive can be in a discontinuous pattern that can be formed in multiple ways. For example, a discontinuous pattern can be applied as a pre-cut double sided medical tape or transfer adhesive. Alternatively, the adhesive can be applied as a liquid adhesive in a discontinuous pattern using methods such as gravure coating. A variety of patterns may be used including circles, ovals stripes or polygons, such as rectangles, squares, triangles etc. The hexagonal pattern depicted in FIG. 11 is conveniently applied, but not required. The pattern need not be symmetrical. In addition, the discontinuous adhesive pattern may extend to the periphery of the device or a continuous pattern adhesive border can be applied around the perimeter of the engaging layer. In addition, two or more adhesives may be used in combination to optimize adherence under different conditions. For example a first adhesive could provide greater adherence under dry conditions and a second adhesive provide greater adherence under moist conditions.

In an alternative embodiment, the adhesive can be applied in a continuous pattern and subsequently made discontinuous. For example, holes can be formed through the entire thickness of an NSD after a continuous adhesive is applied to the engaging layer, thus forming a discontinuous adhesive layer. No particular pattern of holes is necessary. However, preferably, the pattern of the holes is relatively evenly distributed over the entire surface area of the device and the locations of the holes are selected to avoid penetration through the lift members. As discussed above, the shape of the holes forming the discontinuous pattern can be round, oval, polygons etc. The ratio of adhesive area: non-adhesive area of a discontinuous adhesive pattern can be about 90:10 to 10:90, typically about 30:70 to 70:30, and in some embodiments, about 40:60-60:40.

Without being limited to a single theory, it is believed that in addition to permitting passage of perspiration to the exterior surface of the device, the discontinuous adhesive pattern, particularly in the form of holes facilitates malleability of the device to permit the device to more readily conform to the surface contours of the vestibular free wall without loss of adherence or reduced support of the device.

The NSD can include a surface layer. The surface layer is the layer farthest from the soft tissues of the animal. The side of the surface layer closest to the soft tissue of the animal can include an adhesive to adhere the surface layer to the support layer, to the top side of the engaging layer that may be exposed between lift members, or to the pad layer if used. The surface layer can provide additional support to the vestibular wall and help maintain unity of the components of an NSD. A suitable surface material can be breathable or non-breathable and typically includes a biocompatible adhesive. An example of a breathable material suitable as a surface layer is No. 1533 available from 3M Inc., St. Paul, Minn. One preferred non-breathable surface material is No. 9906T non-woven medical tape available from 3M Co., St. Paul, Minn. This material has been found to advantageously flex with the surface contour changes of the vestibular wall thus reducing the likelihood that the device will disengage from the animals nose, for example, during strenuous exercise. Preferably, because this material is non-breathable, holes are created through the entire thickness of the device to provide for passage of moisture and further cooperative malleability of the NSD.

The support layer can mount directly to the engaging layer. However, the NSD can also include a "pad layer" applied between the engaging layer and support layer. Alternatively, the pad layer can be applied between the surface layer and the support layer. An adhesive may be applied to both sides of the pad layer, only a single side or not all. That is the pad layer can be "free floating."

In another embodiment, a partial pad layer can be applied. According to this embodiment, the pad layer can be applied between the support layer and the surface layer. The pad layer can be adhered to the layers on either side of the pad layer or only to the layer on one side. For example, the pad layer can be applied between the support layer and engaging layer, but only adhered to the engaging layer and regions of the surface layer between individual lift members.

The pad layer can be formed of any suitable known material. One preferred material is a polyester material that allows the skin of the vestibular wall beneath the device to breathe. An example of a suitable pad layer is the product SONTARA® (style nos. 8004, 8005, 8027 etc.) available from E.I. DuPont Nemours & Co., DuPont Nonwoven Division, Old Hickory, Tenn. SONTARA® is a nonwoven, spunlaced, breathable polyester fabric.

If no pad layer is used, the support layer can mount directly to the engaging layer using a double sided adhesive. Alternatively, the lift members can be adhered to a non-adhesive side of the engaging layer, or to a nonadhesive pad layer using a double sided adhesive such as 3M 1509, 3M Inc., St. Paul, Minn. Other arrangements are foreseen. For example, the adhesive of the engaging layer can be applied between the support layer and surface layer. According to this embodiment, the engaging layer adheres to the animal's nose between individual lift members that are not adhered to the animal.

The surface layer can include an ornamental design color, pattern, logo etc. if desired. Alternatively, an ornamental veneer layer can be applied to the exposed surface of a surface layer or support layer.

The engaging layer, surface layer, or pad layer (if used) can closely follow the external contours defined by the support layer. Alternatively, the periphery of the engaging or other layers can extend beyond the contours defined by the support layer. In a preferred embodiment, extending the periphery of the engaging layer beyond the contours defined by the support layer can provide improved engagement of the NSD to the animal's nose. In one embodiment a margin region of about 0.5 cm to 5 cm, preferably about 2-3 cm of engaging layer extends beyond the support provided by the support layer. If present, the surface layer typically has the same perimeter dimensions as the engaging layer.

Generally, the overall thickness of the device is uniform. Some variation in thickness can occur due to differences in thickness of those regions of the device including the support members and those regions having spacing between support members.

The inventors also recognize that single or multiple lift members without a unifying layer (e.g., surface layer or engaging layer) can be used. According to this embodiment, an engaging layer, such as a previously described adhesive, can be applied to the lift member. One or more lift members can then be applied directly to the animals nose. While this embodiment may address the unique physiological and anatomical aspects of an animals nose as disclosed herein, the application and removal of the support members will be cumbersome. In addition, the support provided by the surface layer or engaging layer in the regions between the lift members will be lost.

DETAILED DESCRIPTION OF ILLUSTRATED EMBODIMENT

Anatomical reference points and embodiments of an NSD according to the invention will be described in detail with reference to the drawings using the horse as an example. Like reference numerals represent like parts and assemblies throughout the several views. Reference to the drawings is not intended to limit the scope of the invention to the illustrated embodiments.

Figure 1C:
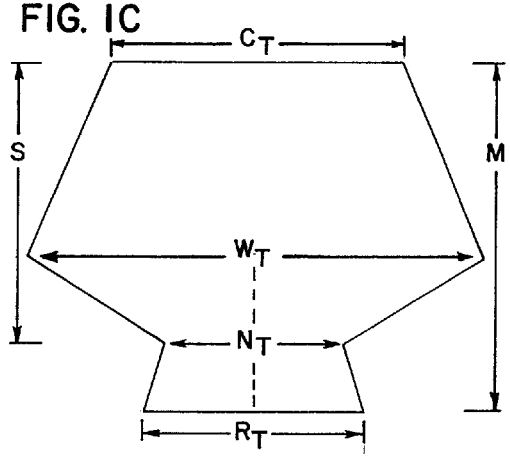
FIG. 1c is a top view of a third configuration of an embodiment of an NSD which incorporates the functional aspects of the invention.
Figure 1F:
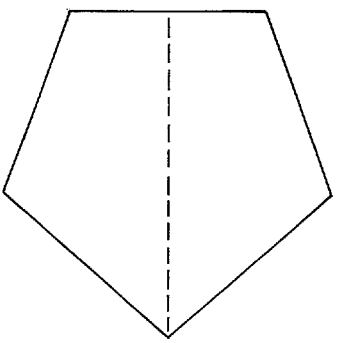
FIG. 1f is a top view of a sixth configuration of an embodiment of an NSD which incorporates the functional aspects of the invention.
Figure 1G:
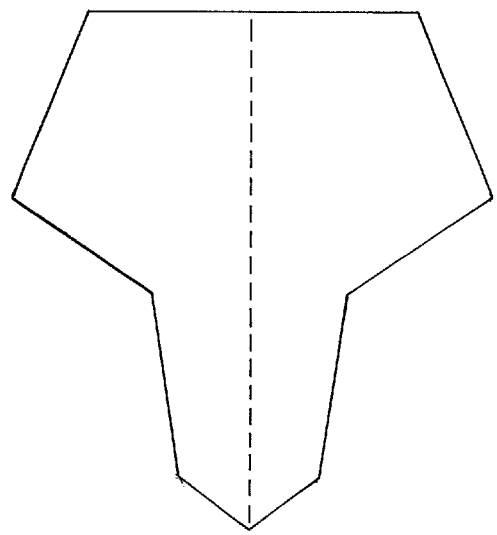
FIG. 1g is a top view of a seventh configuration of an embodiment of an NSD which incorporates the functional aspects of the invention.
Figure 1H:
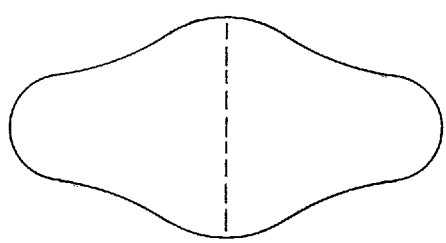
FIG. 1h is a top view of an eighth configuration of an embodiment of an NSD which incorporates the functional aspects of the invention.
Figure 1I:
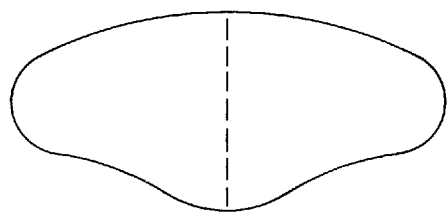
FIG. 1i is a top view of a ninth configuration of an embodiment of an NSD which incorporates the functional aspects of the invention.

FIG. 1*a-i* are each a top view of a configuration of an embodiment of an NSD which incorporates the functional aspects of an NSD as disclosed herein. The embodiments shown are exemplary and are not intended to limit the scope of configurations that incorporate the principles of the invention. FIG. 1*c* shows various dimensions which can be used to characterize an NSD according to the invention wherein letters followed by a subscript "T" are the transverse dimensions including $C_T$ is the caudal edge transverse dimension, $R_T$ is the rostral edge transverse dimension, $N_T$ is the narrowest part transverse dimension and $W_T$ is the widest part transverse dimension. S is the rostral-poll dimension of the side piece and M is the rostrum poll dimension of the midline region.

Figure 2:
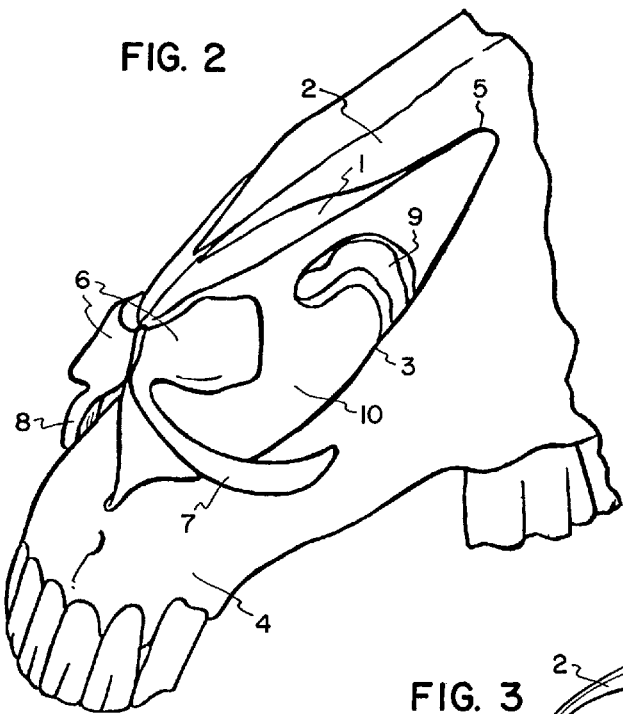
FIG. 2 is a perspective view of the bony and cartilaginous anatomy of the rostrum nasal cavity of the horse.
Figure 3:
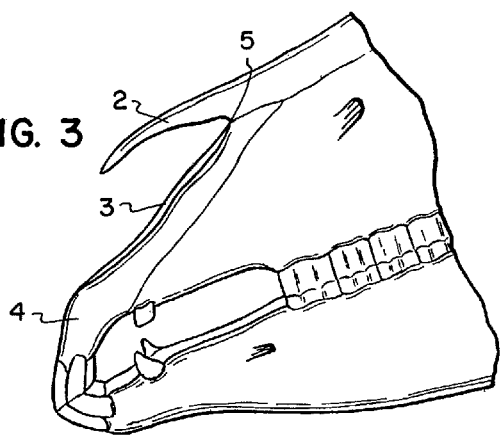
FIG. 3 is a profile view of the bony anatomy of the rostral nasal cavity of the horse.
Figure 4:
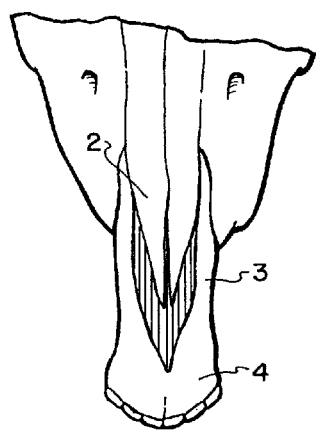
FIG. 4 is a dorsal or top view of the bony anatomy of the rostral nasal cavity of the horse.

Bony anatomical structures which surround the vestibule free wall in the horse that is supported by a device of the invention is described with reference to FIGS. 2-4. FIG. 2 is a perspective view of the bony and cartilaginous structures of the rostrum nasal cavity of the horse. FIG. 3 is a profile view of the bony anatomy and FIG. 4 is a top view of the same rostrum anatomy of FIG. 3. FIGS. 3 and 4 do not show cartilaginous anatomy of the adult horse.

The lateral free wall of the vestibule is defined dorsal by the dorsal lateral nasal cartilage 1 which is the lateral most aspect of the nasal bone 2. The ventral border of the vestibule free wall is defined by the dorsal free wall 3 of the incisive bone 4. The caudal aspect of the vestibule free wall is defined by the intersection 5 of the nasal 2 and incisive 4 bones. The rostrum aspect of the vestibule, free wall is bordered by the nostril (not shown) which is supported dorsal by the lamina 6 and ventral by the corn 7 of the allure cartilage 8. The medial accessory cartilage 9 and the lamina 6 of the allure cartilage support the "false" nostril of the horse. The cartilaginous rostrum nasal septum 10 is shown in FIG. 2.

FIGS. 5-7 illustrate three different embodiments of an NSD (15, 16, 17) according to the invention. The surface layer is removed in each of these figures to expose the top side of the support layer 20 and the top side of the pad layer 21 which covers the engaging layer (not shown). The support layer 20 includes transverse lift members 22 in FIGS. 5-7 and longitudinal lift members 23 in FIG. 7. The lift members 22 of FIG. 5 are narrower but greater in number than the lift members 22 of FIG. 6. In the embodiment of FIG. 2. the transverse dimension of the lift members range from 9 cm to 14 cm, the width of the transverse members is about 0.6 cm, the spacing between members is about 0.6 cm and the thickness of the lift members is about 0.14 inches. In the embodiments of FIGS. 5-7, the peripheral contours of the pad layer (and engaging layer) extend beyond the lift members.

As shown in FIGS. 5-7, an NSD includes a first side piece 24 and a second side piece 25 that intersect at the midline 26 of the midline region 26*a* of the device. In use, the rostral end 27 of the device is oriented towards the apex of the nose and the caudal end 28 is oriented towards the eyes of the animal.

In FIG. 5, the midline rostral-poll dimension M at the midline 26 is at least equal to the side piece rostral-poll dimension S of side pieces 24 and 25. Also as shown in the embodiments of FIGS. 5-7, preferably, the rostral-poll dimension of the NSD at the midline M is greater than the rostral-poll dimensions S of the first or second side pieces 24, 25. In FIG. 7, the NSD includes a rostrally extending center piece or "tongue" 29 that can extend rostrally to engage the nose between the nostrils.

Figure 9:
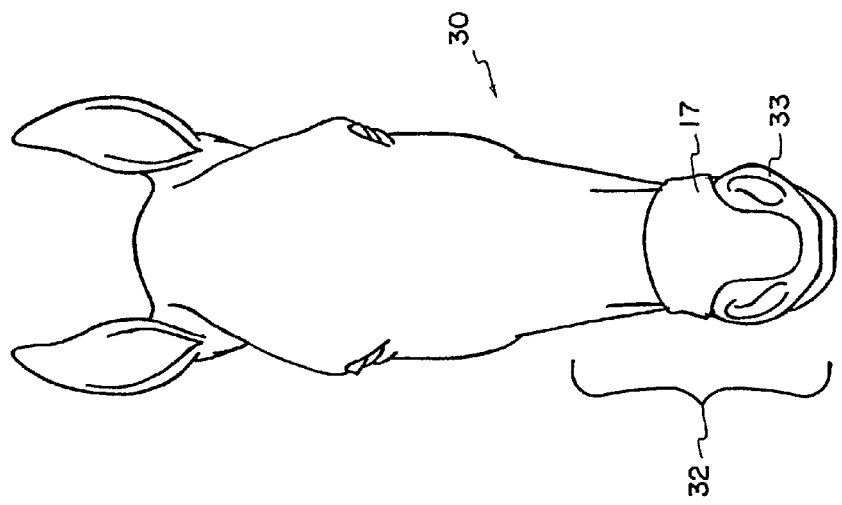
FIG. 9 is a front view of a horse having an embodiment of an NSD of FIG. 7 secured to its nose.
Figure 8:
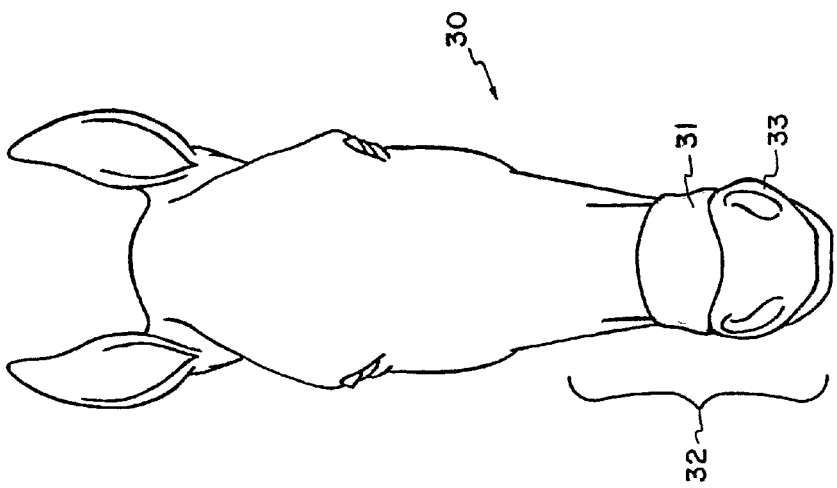
FIG. 8 is a frontal view of a horse having an embodiment of an NSD of FIG. 5 or 6 secured to its nose.

In use, an NSD is secured to the animal's nose oriented generally as shown in FIGS. 8 and 9. FIG. 8 is a front view of a horse 30 having an embodiment of an NSD 31 having an external configuration as shown in FIGS. 5 and 6 (15 and 16, respectively) secured to the nose 32. FIG. 9 is a front view of a horse 30 having an embodiment of an NSD 17 as shown in FIG. 7 secured to its nose 32. As can be seen in FIG. 9, the tongue 29 of the NSD 17 extends between the nostrils 33 of the horse 30.

FIG. 10 is an exploded perspective view of the components making up an embodiment of an NSD 15 as shown in FIG. 5. According to this embodiment, the engaging layer 40 includes an adhesive surface 41 to secure the NSD 15 to an animal's nose. A pad layer 42 is adhered to the engaging layer 40. The pad layer 42 can have an adhesive layer or be adhesive free. In the embodiment shown, the engaging layer 40 is a double sided adhesive such that the top side 43 of the engaging layer will adhere to the pad layer 42. The support layer 44 includes lift members 45. The lift members 45 can be adhered to the pad layer 42 using, for example, a double sided adhesive 46. A surface layer 47 can be applied over the support layer 44 to provide unity, additional strength or a "canvas" for applying an ornamental design to the device. Suitable materials for each of the layers have been described previously. The releasable liner for protecting the adhesive surface 41 of the engaging layer is not shown.

FIG. 11 illustrates the engaging layer 110 of another embodiment of an NSD 100 with the releasable liner removed. According to this embodiment, a discontinuous adhesive pattern 101 is applied to the NSD 100 as a pre-cut medical tape or transfer adhesive or applied as a printed liquid adhesive. As described earlier, a polygon adhesive pattern 104 is one of several suitable discontinuous adhesive patterns. While the illustrated embodiment does not include holes, the areas void of adhesive 102 in the adhesive pattern 101 provide for perspiration to pass through a breathable or non-breathable surface layer to the surface of the NSD. It is believed that areas void of adhesive 102 of the adhesive pattern 101 of the engaging layer 110 facilitates engagement of the NSD 110 to the mobile contours of the vestibular wall of some animal's noses, such as a horse. However, it is also foreseen that a pattern similar to that shown in FIG. 11 can include two different adhesives. That is, a first adhesive could be applied as the adhesive pattern 104 and second adhesive applied in regions 102. The two different adhesives could provide adhesive function under different conditions. For example, the first adhesive may provide greater adherence to the nose when the nose is dry and the second adhesive could provide greater adherence when the nose is wet from perspiration. In addition, rather than extending the adhesive pattern to the peripheral edge 109 of the NSD, the engaging layer 110 can include a continuous adhesive border around the perimeter of the NSD. Such a border can be about 0.5 to 5 cm, typically about 2-3 cm wide.

Figure 12:
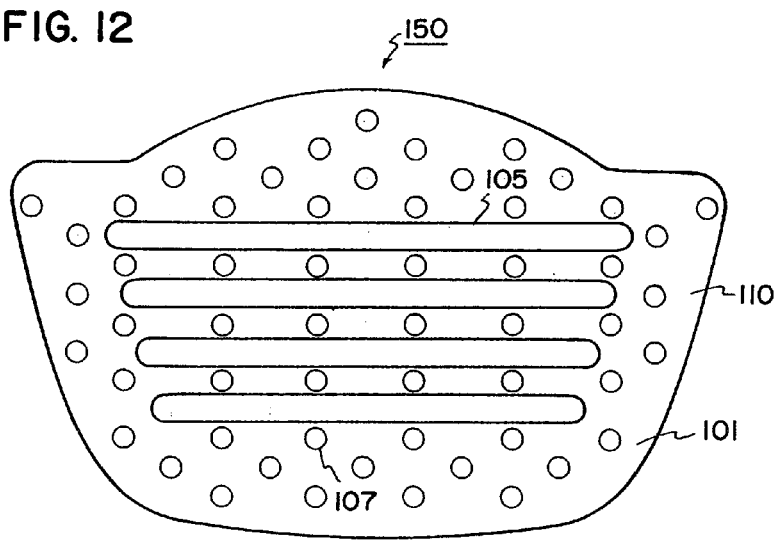
FIG. 12 is a bottom plan view of an embodiment of an NSD having holes throughout the thickness of the device.

FIG. 12 illustrates a bottom plan view of another embodiment of an NSD 150 having a discontinuous adhesive pattern 101 of the engaging layer 110. The releasable liner has been removed. In this embodiment, the discontinuous adhesive pattern 101 is provided by creating holes 107 through the entire thickness of the device. Note that the holes 107 preferably do not pass through the lift members 105. In addition to enhancing the ability of the device 150 to adapt to contour changes of the external surface of the vestibular wall, it is believed that holes 107 provide for passage of perspiration or other moisture from the surface of the animals nose to the external surface of the device 150. The ability for moisture to pass external to the device further reduces the chance of the device 150 disengaging from the nose. As discussed earlier, the shape of the holes is not limited to round.

Figure 13:
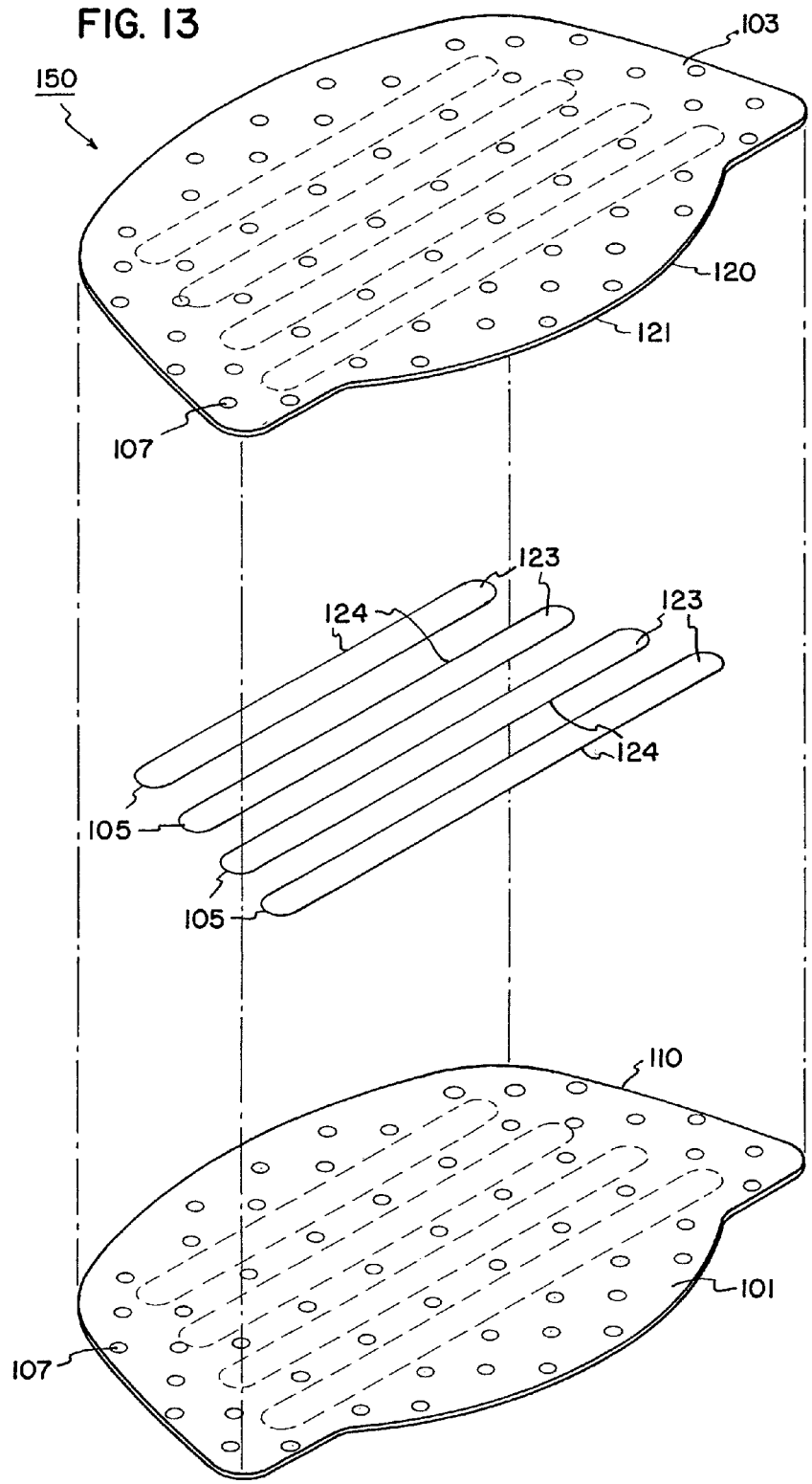
FIG. 13 is an exploded perspective view of the NSD shown in FIG. 12.

FIG. 13 is an exploded perspective view of the NSD 150 of FIG. 12. This embodiment includes a surface layer 103 having an adhesive 120 on the underside 121 of the surface layer 103 for adhering the surface layer 103 to the top side 123 of the lift members 105. One suitable material for the lift members 105 is 1400A MYLAR® (i.e., 1400 gauge MYLAR® which is about 350 micron or 14 mils) available from DuPont, Wilmington, Del. A presently preferred surface material 103 is No. 9906T non-woven medical tape available from 3M Co., St. Paul, Minn. The engaging layer 110 can be applied as a liquid adhesive to the underside 121, 124 of the surface layer 103 and lift members 105, respectively. Alternatively the engaging layer can be applied to the underside 121, 124 of the surface layer 103 and lift members 105, respectively, as a double sided medical tape or transfer adhesive. In one embodiment, two layers of No. 1524 transfer adhesive, available from 3M Co., St. Paul, Minn., provide the adhesive for the engaging layer 110.

Figure 14:
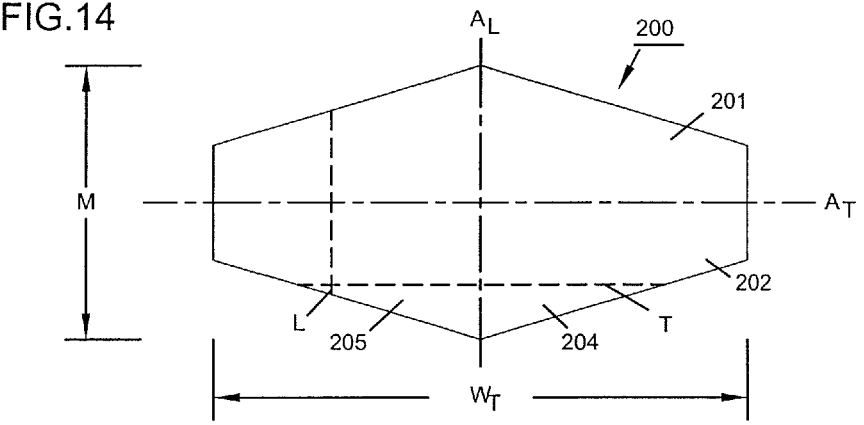
FIG. 14 is a diagrammatic representation of a configurational appearance for an NSD according to the invention having two axes bilateral symmetry.

In another embodiment, an NSD according to the invention provides a bilaterally symmetrical NSD across two dimensional axes of the device. Referring to FIG. 14, a general configuration for an NSD according to this embodiment is diagrammatically illustrated. As illustrated, NSD 200 has a transverse axis $A_T$ through the widest transverse dimension $W_T$. NSD 200 also has a longitudinal axis $A_L$ through the longest rostral-caudal dimension M. Thus, although other longitudinal dimensions L and transverse dimensions T are present, the greatest dimension in either the longitudinal or transverse direction is at the axes.

According to this embodiment, the NSD is bilaterally symmetrical on opposing aspects of transverse axis $A_T$. That is, the upper surface 201 of NSD 200 looks substantially identical to the bottom surface 202. In addition, the NSD is bilaterally symmetrical on opposite sides of longitudinal axis $A_L$ such that the right surface 204 is substantially identical to the left surface 205. It will be appreciated that each axes $A_T$ and $A_L$ bisects the device into bilaterally symmetrical halves in their respective dimensions.

The general appearance of NSD 200 of FIG. 14 can include any of the structural features or components of other NSDs disclosed herein, but, in addition to other advantages, this configuration provides for ease of application and reduced likelihood of malfunction due to improper positioning. Specifically, the device provides structural features in a configuration which can be placed on the nose in the position illustrated in FIG. 14 or rotated 180° therefrom.

In addition, the two axes bilaterally symmetrical devices can include all structural aspects, components, or functional features described above for other NSD embodiments, but within varying appearances as illustrated in FIGS. 15-40 as described below.

Figure 15:
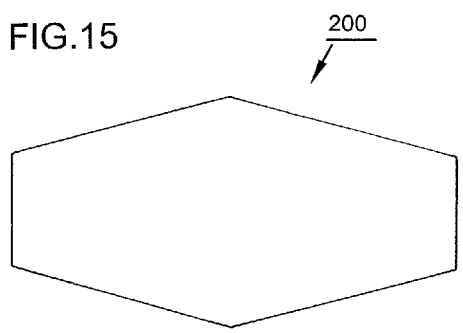
FIG. 15 is a top side view of one appearance of an NSD having two axes bilateral symmetry.
Figure 16:
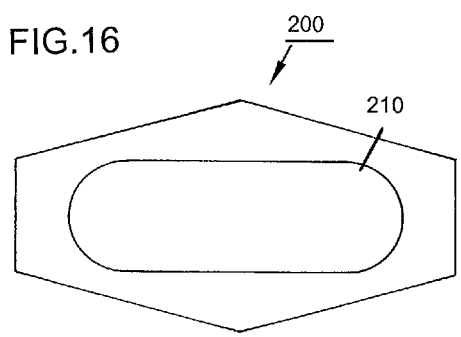
FIG. 16 is bottom side view of the NSD of FIG. 15.
Figure 17:
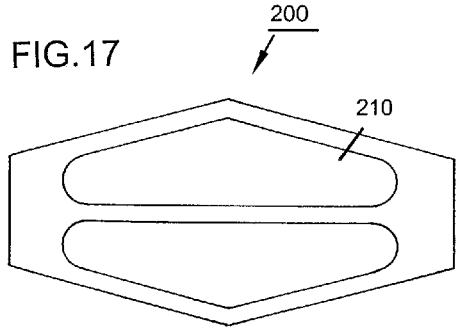
FIG. 17 is an alternative embodiment of a bottom side view of the NSD of FIG. 15.
Figure 18:
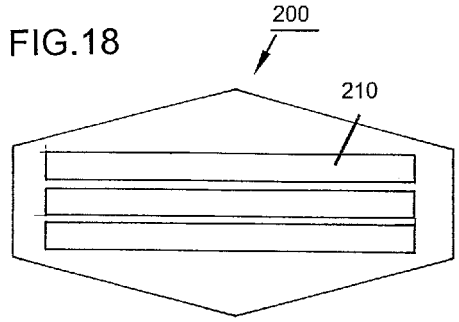
FIG. 18 is an alternative embodiment of a bottom side view of the NSD of FIG. 15.

FIG. 15 illustrates a top side view of one appearance for the configuration of a two axes bilaterally symmetrical NSD as described above with reference to FIG. 14. FIG. 16-18 illustrate a bottom side view of the embodiment of FIG. 15 with varying numbers of support members 210 as described earlier. An intermittent adhesive pattern can be used as described. Holes may also be placed through the device, preferably not located in or through the lift members.

Figure 34:
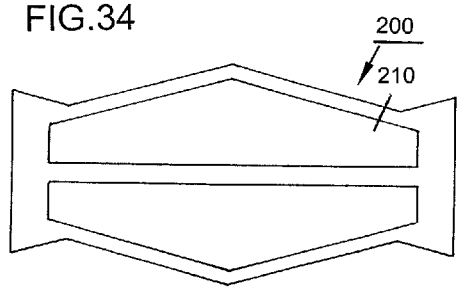
FIG. 34 is an alternative embodiment of a bottom side view of the NSD of FIG. 32.
Figure 35:
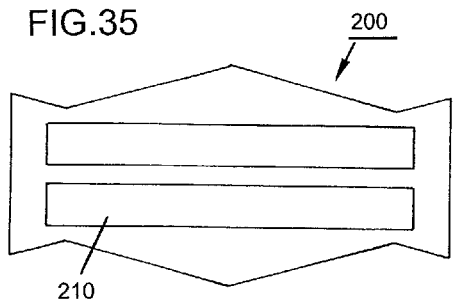
FIG. 35 is an alternative embodiment of a bottom side view of the NSD of FIG. 32.
Figure 36:
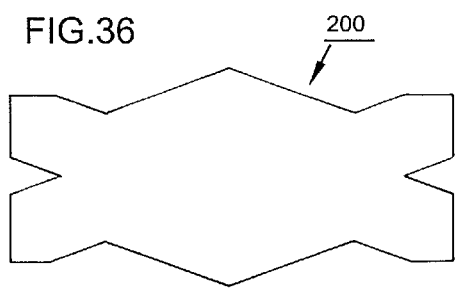
FIG. 36 an alternative embodiment of a top side view of an NSD having two axes bilateral symmetry.
Figure 37:
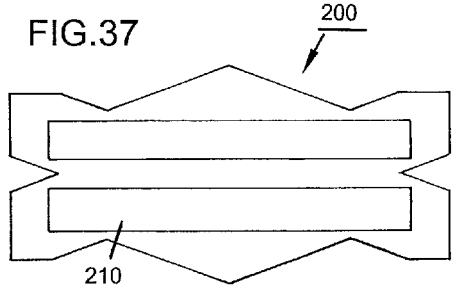
FIG. 37 is bottom side view of the NSD of FIG. 36.
Figure 38:
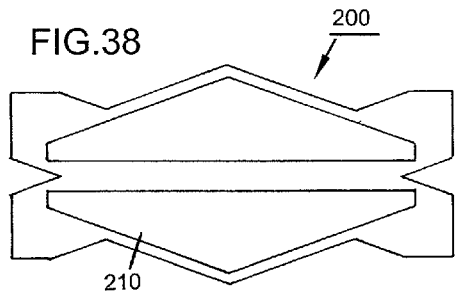
FIG. 38 is an alternative embodiment of a bottom side view of the NSD of FIG. 36.
Figure 39:
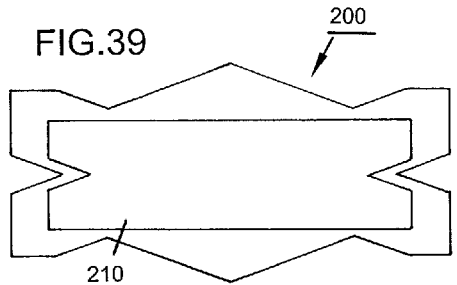
FIG. 39 is an alternative embodiment of a bottom side view of the NSD of FIG. 36.
Figure 40:
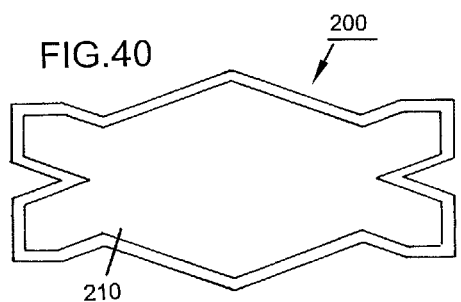
FIG. 40 is an alternative embodiment of a bottom side view of the NSD of FIG. 36.

FIG. 19 is a top side view and FIGS. 20-22 are bottom side views of an alternative appearance of an NSD containing the configurational features described. FIG. 23 is a top side view and FIGS. 24-26 are bottom side views of an alternative appearing embodiment. FIG. 27 is a top side view and FIGS. 28-31 are bottom side views of another alternative appearing embodiment. FIG. 32 is a top side view and FIGS. 33-35 are bottom side views of yet another alternative appearing embodiment. FIG. 36 is a top side view and FIGS. 37-40 are bottom side views of another alternative appearing embodiment of an NSD according to the invention.

Thus, each of the foregoing embodiments illustrated in FIGS. 15-40 can include some or all of the structural features or arrangements of other NSDs disclosed herein but with different ornamental appearances. The side view of each of the embodiments is substantially void of any ornamental features. In addition, the lift members can be of the same number, size, shape, material, material thickness, etc. as previously described. In addition, construction features, component layers, adhesive features, holes, intermittent adhesive patterns, etc. can be used.

Figure 41:
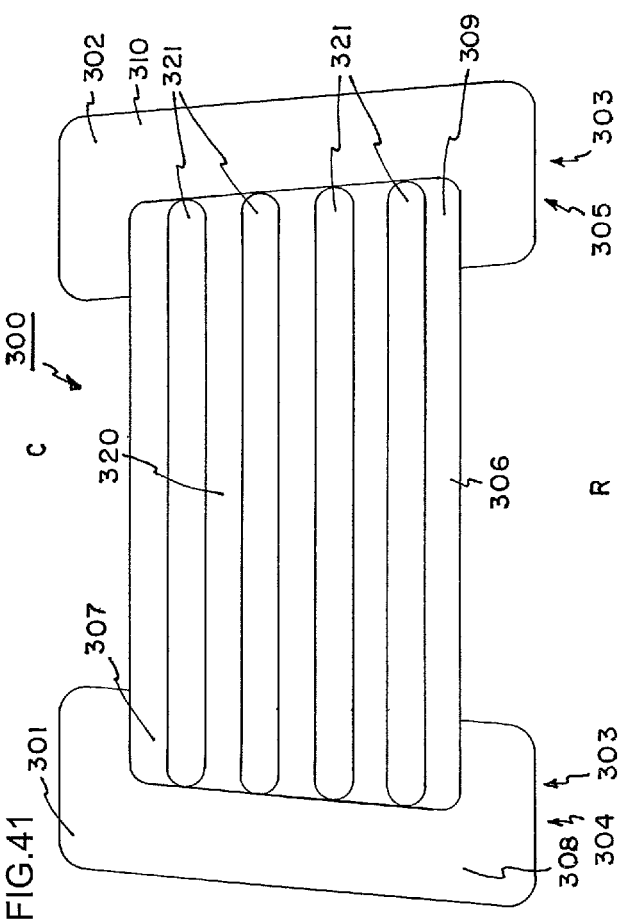
FIG. 41 is an alternative embodiment of an NSD according to the invention.
Figure 42:
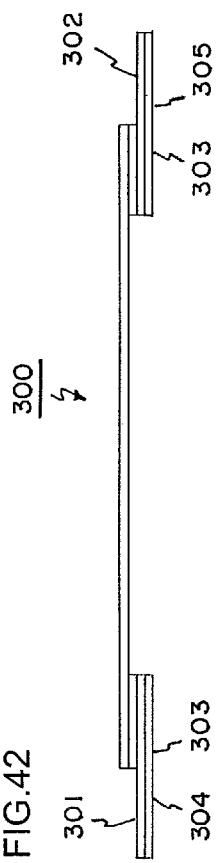
FIG. 42 is a rostral end view of the NSD of FIG. 41.

In another embodiment, an NSD 300 according to the invention can be provided in component parts, some of which are reusable. FIG. 41 is a top plan view of one such embodiment and FIG. 42 is an end-on view of the embodiment of FIG. 41 looking from the rostral aspect R. According to this embodiment, NSD 300 includes a first side piece 301 for engaging to a first lateral vestibular wall and a second side piece 302 for engaging a second lateral vestibular wall. An engaging layer 303 including adhesives and adhesive systems as described earlier can be applied to the bottom surfaces 304 or 305 of side pieces 301 and 302, respectively, for adhering the side pieces to the lateral vestibular walls. Bridge piece 306 is configured to traverse the animal's nose and attach at a first lateral region 307 to the first top side 308 of first side piece 301 and attach at a second lateral region 309 to a second top side 310 of second side piece 302. The bridge 306 can attach to the side pieces 301 and 302 using known systems such as velcro, buckles, zippers, snaps, hooks, hook and loops, snaprings, clips or other similar attachment providing for reusable attachment of bridge piece 306 to the side pieces. The side pieces 301 and 302 will typically be replaced after each use.

It will be appreciated that bridge piece 306 includes a surface material 320 which keeps individual lift members 312 in a fixed arrangement relative to one another. The components of the surface layer and lift members can be as previously described. Alternative materials consistent with the functional requirements for an NSD of the invention can also be used. One, two, three, four or more lift members 321 can be used as needed. Holes may also pass through the bridge piece 306 which preferably do not pass through lift members 321.

Side pieces 301 and 302 may or may not include lift members and also may or may not include holes. If used, one or more lift members can be used which are oriented parallel, perpendicular or oblique to the lift members of bridge piece 306.

Figure 43:
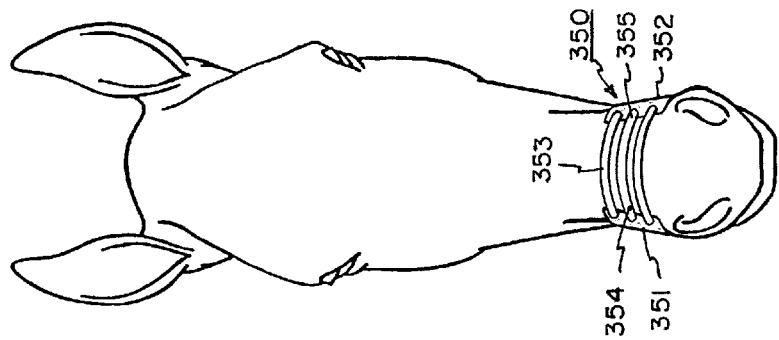
FIG. 43 illustrates an alternative embodiment of an NSD positioned over the lateral vestibular walls of a horse.

FIG. 43 illustrates another embodiment of an NSD 350 having a first side piece 351 and a second side piece 352 substantially as described for NSD 300 above. However, in contrast to bridge piece 306, the bridge piece of embodiment 350 comprises at least two, typically three and optionally more, independent lift members 353. Each lift member can attach at its lateral region 354, 355 to side pieces 351 and 352 as described for NSD 300.

Figure 44:
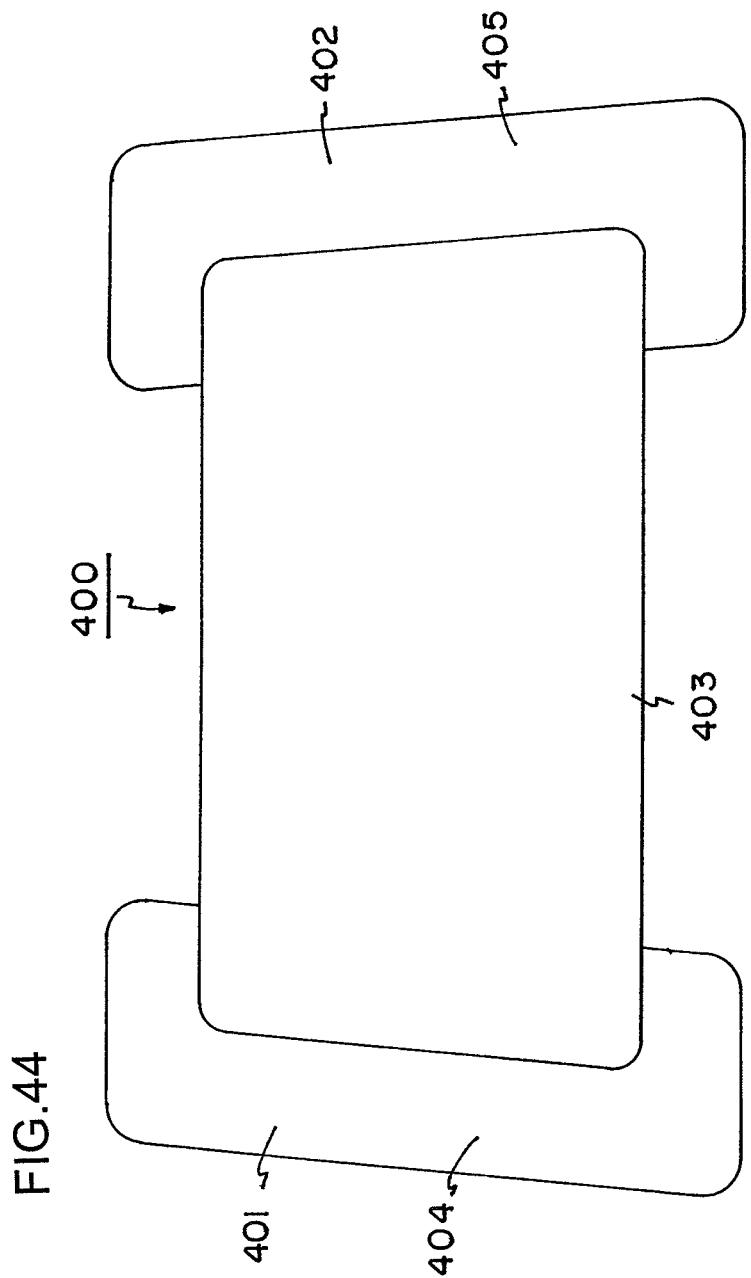
FIG. 44 is an alternative embodiment of an NSD according to the invention.

FIG. 44 illustrates another embodiment of an NSD 400 having a first side piece 401 and a second side piece 402 substantially as described for NSDs 300 and 350. However, bridge piece 403 comprises a single unit piece which traverses the nose and attaches at its lateral edges 404 and 405 to first side piece 401 and second side piece 402 as described above. Hence, for each of the NSD embodiments 300, 350 and 400, the first and second side pieces can be discarded after use and bridge pieces 306, 353 and 403 can be reused. With each use, the operator can apply the lateral regions to the first and second side pieces with a selected amount of tension for a desired amount of support for the lateral vestibular wall.

An NSD as disclosed herein provides support for the nasal passages of an animal. The support provides for increased airflow at rest and during exercise. The air flow facilitating affects of an NSD can be determined by various methods including measurement of air flow rates, driving pressure for flow and impedance to air flow. Air flow rates can be measured by attaching a pneumotachograph to a face mask worn by an exercising horse. Driving pressure for flow can be measured by passing a catheter via the nares to the pharynx. From the pressure and flows, impedance to air flow can be calculated. Flow volume loops may demonstrate reduction of dynamic collapse of the nasal passages. It is believed that some embodiments of an NSD as described herein will provide at least about 5-10% reduction in inspiratory impedance, in some embodiments at least about 15-25%, and in some embodiments over a 25% reduction. During preliminary studies, one horse showed over 40% reduction in inspiratory impedance when wearing an NSD of the invention. A detailed description of methods useful for measuring air flow affects of an NSD are described in Lumsden et al., "Use of Flow-Volume Loops to Evaluate Upper Airway Obstruction in Exercising Standardbreds," *AJVR*, 54(5):766-775 (May 19, 1993).

In a performance horse, an NSD can be particularly beneficial for reducing the chance of exercise induced respiratory conditions. For example, the inventors foresee use of an NSD to reduce the chance of exercise induced pulmonary hemorrhage (EIPH) or "bleeders". The ability to decrease the incidence of this condition without the use of pharmacological agents will provide a major benefit to the horse industry. In addition, an NSD may also facilitate air flow in horses afflicted with partial or full recurrent laryngeal nerve dysfunction ("roarers") or dorsal displacement of the soft palate. The device has been shown to reduce the noise associated with recurrent laryngeal nerve dysfunction in some horses.

In another embodiment, the invention provides therapeutic devices for treating conditions amenable to the delivery of magnetic, electromagnetic, thermal (hot or cold), ultrasonic or other energy emitting modality. The device could also provide for delivery of a pharmaceutical agent. According to this embodiment, the surface layer and engaging layer components and constructions herein described for an NSD can be used. However, in contrast to previously described devices, in the present devices, the support layer is supplanted by, or supplemented with, a therapeutic layer. In addition, the configurational appearance can vary depending on the size or region of the body to which it is desired to deliver the therapeutic energy.

According to this embodiment, the therapeutic layer can include wafer shaped magnets, electromagnets, ultrasound transmitters, thermal emitters or other known therapeutic modality. For example, in one embodiment, the lift members can be supplanted by placement of thin magnets which deliver magnetic energy to a localized region of the body over which the device is placed. In general, preferred components of the therapeutic layer, such as magnets, are flexible to conform to the location of the body where the device will be applied, but lack significant elasticity or shape memory which would act to conform the shape of the body region to the engaging surface of the device. The adhesive surface can be continuous or intermittent on one side of the therapeutic layer. A surface layer may optionally be used.

In some embodiments, the device can include a surface layer, a therapeutic layer and an adhesive layer. The surface layer can be configured to include a border which extends sufficiently around the perimeter of the therapeutic layer. The adhesive layer can then be applied over the therapeutic layer and the perimeter border to provide adhesive engagement of the device to a selected location of the patient's body. As described for the support layer above, an adhesive can be used to adhere the therapeutic layer to the surface layer. Examples of appearances of suitable configurations can be understood by reference to FIGS. 5-8, 10-13, and 15-44 wherein the lift members would be replaced by the particular therapeutic delivery apparatus.

Many of the adhesive systems disclosed herein are advantageous for adhering to the body. In addition, by adjusting the moisture absorbing characteristics of the adhesives used, such as by addition of a hydrocolloid, such as carboxymethylcellulose, polyacrylamide, or similar composition, the ability to maintain position in the presence of sweat or other fluids will be increased. In addition to other adhesives, suitable adhesives include adhesives of a type used to maintain EKG patches on a human or animal body. In an alternative embodiment, the therapeutic deliver apparatus can be inserted into a pouch made from plastic, PTFE, fabric or other suitable material having a surface coated with an engaging layer as disclosed herein.

Examples of conditions which can be treated by placement of a herein disclosed therapeutic device at or near the location of the condition include: acute or chronic inflammation, nonunion fractures, splints, muscle soreness, tendon injuries, etc.

It will be apparent to one of ordinary skill in the art that many changes and modifications can be made in the invention without departing from the spirit or scope of the appended claims.

What is claimed is:

1. A nasal support device sized and configured for supporting tissues overlying first and second nasal passages, the support device comprising:

a nasal support structure having a midline, the nasal support structure being symmetric about the midline;

the nasal support structure defining first and second lateral boundaries positioned on opposite sides of the midline, each of the first and second lateral boundaries having a first rounded section, a second rounded section and a third rounded section;

the nasal support structure defining a first transverse dimension that extends between the first rounded sections of the first and second lateral boundaries, a second transverse dimension that extends between the second rounded sections of the first and second lateral boundaries, and a third transverse dimension that extends between the third rounded sections of the first and second lateral boundaries, the second transverse dimension being positioned at an intermediate location between the first and third transverse dimensions;

the first transverse dimension being larger than the third transverse dimension;

the nasal support structure including a lift structure configured to reduce the draw of the supporting tissues inward toward the nasal passages during respiration, the lift structure including at least a first lift member having a length that extends across the midline, the first lift member having first and second lateral extents extending away from the midline; and the nasal support structure including an adhesive surface having portions that extend beyond the lateral extents of the first lift member, the adhesive surface being configured for attaching the nasal support device to a nose, and the nasal support device being configured such that the first, second and third transverse dimensions overlie the nose when the nasal support device is attached to the nose, wherein the nasal support structure includes a fourth transverse dimension measured between the first and second lateral boundaries at a location between the first and second transverse dimensions and a fifth transverse dimension measured between the first and second lateral boundaries at a location between the second and third transverse dimensions, the fourth transverse dimension being smaller than the first and second transverse dimensions and the fifth transverse dimension being smaller than the second and third transverse dimensions.

2. The nasal support device of claim 1, wherein the midline extends in a caudal to rostral orientation.

3. The nasal support device of claim 2, wherein the nasal support device has a rostral end opposite a caudal end and the first and third transverse dimensions are located adjacent opposite ends of the nasal support device.

4. The nasal support device of claim 3, wherein the first dimension is located adjacent the caudal end of the nasal support device and the second dimension is located adjacent the rostral end of the nasal support device.

5. The nasal support device of claim 1, wherein the first, second and third rounded sections have convex curvatures.

6. The nasal support device of claim 5, wherein the first and second lateral boundaries define concave curvatures at the fourth and fifth transverse dimensions.

7. The nasal support device of claim 1, wherein the first transverse dimension is larger than the second transverse dimension.

8. The nasal support device of claim 1, wherein the first and second lateral boundaries extend:
   inwardly from the first rounded sections to a first narrowed region at the fourth transverse dimension;
   outwardly from the first narrowed region to the second rounded sections;
   inwardly from the second rounded sections to a second narrowed region at the fifth transverse dimension; and
   outwardly from the second narrowed region to the third rounded sections.

9. The nasal support device of claim 1, wherein the nasal support structure defines first and second longitudinal boundaries, and where in the first and third rounded sections are positioned at the first and second longitudinal boundaries, respectively.

10. A nasal support device sized and configured for supporting tissues overlying first and second nasal passages, the support device comprising:
   a nasal support structure having a midline, the nasal support structure being symmetric about the midline;
   the nasal support structure defining first and second lateral boundaries positioned on opposite sides of the midline, each of the first and second lateral boundaries having a first rounded section, a second rounded section and a third rounded section;
   the nasal support structure defining a first transverse dimension that extends between the first rounded sections of the first and second lateral boundaries, a second transverse dimension that extends between the second rounded sections of the first and second lateral boundaries, and
   a third transverse dimension that extends between the third rounded sections of the first and second lateral boundaries, the second transverse dimension being positioned at an intermediate location between the first and third transverse dimensions;
   the first transverse dimension being larger than the third transverse dimension;
      the nasal support structure including a lift structure configured to reduce the draw of the supporting tissues inward toward the nasal passages during respiration, the lift structure including at least a first lift member having a length that extends across the midline, the first lift member having first and second lateral extents extending away from the midline; and
      the nasal support structure including an adhesive surface having portions that extend beyond the lateral extents of the first lift member, the adhesive surface being configured for attaching the nasal support device to a nose, and the nasal support device being configured such that the first, second and third transverse dimensions overlie the nose when the nasal support device is attached to the nose, wherein the first, second and third rounded sections are defined by rounded projections, and wherein nasal support structure includes a first laterally narrowed region between the first and second transverse dimensions and a second laterally narrowed region between the second and third transverse dimensions.

11. The nasal support device of claim 10, wherein the rounded projections are convex, and wherein the first and second lateral boundaries of the nasal support structure are concave where the nasal support structure is narrowed.

12. The nasal support device of claim 10, wherein the first transverse dimension is larger than the second transverse dimension.

13. The nasal support device of claim 10, wherein the first and second lateral boundaries extend:
   inwardly from the first rounded section to the first narrowed region;
   outwardly from the first narrowed region to the second rounded sections;
   inwardly from the second rounded sections to the second narrowed region; and
   outwardly from the second narrowed region to the third rounded sections.

14. The nasal support device of claim 10, wherein the nasal support structure defines first and second longitudinal boundaries, and where in the first and third rounded sections are positioned at the first and second longitudinal boundaries, respectively.

* * * * *